(12) United States Patent
Cirillo et al.

(10) Patent No.: US 6,852,717 B2
(45) Date of Patent: Feb. 8, 2005

(54) COMPOUNDS USEFUL AS ANTI-INFLAMMATORY AGENTS

(75) Inventors: Pier Francesco Cirillo, Woodbury, CT (US); Daniel R. Goldberg, Redding, CT (US); Abdelhakim Hammach, Danbury, CT (US); Neil Moss, Ridgefield, CT (US); John Robinson Regan, Larchmont, NY (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 76 days.

(21) Appl. No.: 10/143,322

(22) Filed: May 10, 2002

(65) Prior Publication Data

US 2003/0008868 A1 Jan. 9, 2003

Related U.S. Application Data

(60) Provisional application No. 60/291,425, filed on May 16, 2001.

(51) Int. Cl.$^7$ .................. C07D 413/04; C07D 253/02; A61K 31/506; A61K 31/53; A61P 19/02
(52) U.S. Cl. ................ 514/235.5; 514/235.8; 514/236.5; 514/236.8; 514/241; 514/245; 514/252.14; 514/269; 514/272; 514/273; 514/274; 514/342; 514/346; 514/407; 514/459; 544/123; 544/124; 544/140; 544/211; 544/212; 544/219; 544/295; 544/312; 544/319; 544/321; 546/270.7; 546/279.1; 546/291; 548/371.7; 549/292; 549/419
(58) Field of Search ............... 514/235.5, 235.8, 514/245, 252.14, 270, 272, 273, 274, 343, 351, 406, 459; 544/123, 124, 140, 212, 219, 295, 312, 319, 321; 546/270.7, 279.1, 300; 548/372.5; 549/29, 419

(56) References Cited

U.S. PATENT DOCUMENTS

| | | | |
|---|---|---|---|
| 4,435,567 A | 3/1984 | Lugosi et al. |
| 6,211,373 B1 | 4/2001 | Widdowson et al. |
| 6,262,113 B1 | 7/2001 | Widdowson et al. |
| 6,297,381 B1 | 10/2001 | Cirillo et al. |
| 6,319,921 B1 | 11/2001 | Cirillo et al. |
| 6,329,415 B1 | 12/2001 | Cirillo et al. |
| 6,333,325 B1 | 12/2001 | Cirillo et al. |

FOREIGN PATENT DOCUMENTS

| | | | |
|---|---|---|---|
| EP | 0 395 144 | | 10/1990 |
| EP | 0 418 071 A2 | | 3/1991 |
| GB | 1005237 | * | 9/1965 |
| WO | WO 93/24458 | | 12/1993 |
| WO | WO 94/18170 | | 8/1994 |
| WO | WO 97/16442 | | 5/1997 |
| WO | WO 98/52558 | | 11/1998 |
| WO | WO 98/52559 | | 11/1998 |
| WO | WO 99/32106 | | 7/1999 |
| WO | WO 99/32110 | | 7/1999 |
| WO | WO 99/32111 | | 7/1999 |
| WO | WO 99/32455 | | 7/1999 |
| WO | WO 99/32463 | | 7/1999 |
| WO | WO 00/43384 | | 7/2000 |
| WO | WO 00/55139 | | 9/2000 |
| WO | WO 01/36402 | | 5/2001 |

OTHER PUBLICATIONS

Chantry, D., Emerging Drugs, 1999, Chapter 1, pp. 5–13.*
Raine, C.S., et al; Multiple sclerosis: expression of molecules of the tumor necrosis factor ligand and receptor families in relationship to the demyelinated plaque. Rev Nueroi (Paris) 1998: 154:8–9; 577–585.
MA, J.J., et al; Genetic Contribution of the Tumor Necrosis Factor Region in Guillain–Barre Syndrome, Annals of Neurology vol. 44, No. 5, Nov. 1998, pp. 815–818.
Chodorowska, G., Plasma concentrans of IFN–y and TNF–a in psoriatic patients before and after local treatment with dithranol ointment. Journal of the European Academy of Dermatology and Venerology 10 (1998) pp. 147–151.
Nagler, A., et al; Dysregulation of inflammatory cytokines in unrelated bone marrow transplantation. Cytokines, Cellular & Molecular Therapy (1998) vol. 4, pp. 161–167.
Robak, E., et al; Association of Interferon y, Tumor Necrosis Factor a and Interleukin 6 Serum Levels with Systemic Lupus Erythematosus Activity; Archivum Immunologiae et Therapiae Experimentalis, 1998 46, 375–380.
Tashiro, H., et al; Role of cytokines in the pathogenesis of restenosis after percutaneous transluminal coronary angioplasty, Coronary Artery Disease, 2001, vol. 12, No. 2, pp 107–113.
Storz, P., et al; TNF inhibits insulin induced STAT5 activation in differentiated mouse muscle cells pmi28. FEBS Letters 440 (1998) 41–45.
Brown, G., et al; Lymphold Hyperplasia, CD45RBhigh to CD45RBlow T–cell imbalance, and suppression of Type 1 diabetes mellitus result from TNF blockade in NOD NOD-scid adoptive T cell transfer, Diabetologia (1998) 41; 1502–1510.
Bjugstad, K.B., et al; Preventive actions of a synthetic antioxidant in a novel animal model of AIDS dementia, Brain Research 795 (1998) 349–357.
Chou, R.C., et al; Adrenergic regulation of macrophage–derived tumor necrosis factor–a generation during a chronic polyarthritis pain model, Journal of Neuroimmunology 82 (1998) 140–148.

(List continued on next page.)

Primary Examiner—Thomas C. McKenzie
(74) Attorney, Agent, or Firm—Robert P. Raymond; Anthony P. Bottino; Timothy X. Witkowski

(57) ABSTRACT

Disclosed are compounds useful in pharmaceutic compositions for treating diseases or pathological conditions involving inflammation such as chronic inflammatory diseases. Also disclosed are processes of making such compounds.

6 Claims, No Drawings

OTHER PUBLICATIONS

Mueller, G., et al; Is Cytokine Expression Responsible for Differences between Allergens and Irritants? American Journal of Contact Dermatitis, vol. 7, No. 3, Sep. 1996 pp 177–184.

Mitsui, Y., et al; The expression of proinflammatory cytokine mRNA in the sciatic–tibal nerve of ischemia–reperfusion injury. Brain Research 844 (1999) 192–195.

Lemay, S., et al; Prominent and Sustained Up regulation of gp130–Signalling Cytokines and of the Chemokine MIP–2 in Murine Renal Ischemia–Reperfusion Injury. Transplantation vol. 69. No. 5 pp. 959–963.

Boerjesson, A., et al; TNF–a stimulates alveolar liquid clearance during intestinal ischemia–reperfusion in rats. American Journal Physiol. Lung–Cel Mol. Physiol., 278—L3–L12, 2000.

Kurokouchi, K.et al; TNF–a Increases Expression of IL–6 and ICAM–1 Genes Through Activation of NF–kb in Osteoblast–like ROS17/2.8 Cells; Journal of Bone and Mineral Research, vol. 15 No. 8, 1998 pp. 1290 1299.

Higham, M.A., et al; Tumour necrosis factor–a gene promoter polymorphism in chronic obstructive pulmonary disease; European Respiratory Jouranl 2000; 15; pp 281–284.

Takabatake, N., et al; The Relationship between Chronic Hypoxemia and Activation of the Tumor Necrosis Factor–a system in Patients with Chronic Obstructive Pulmonary Disease American Journal Of Respiratory Critical Care Medicine, vol. 161, pp 1179–1184, 2000.

Lee, T.H., Cytokine networks in the pathogenesis of bronchial asthma; implications for therapy Journal of the Royal College of Physicians of London, vol. 32, No. 1, Jan./Feb. 1998.

Lipton, J.M., et al; Peptide Modulation of Inflammamatory Processes within the Brain, Neuroimmunomodulation 1998, pp 178–183.

Li, D., et al; Kinetics of tumor necrosis factor a in plasma and the cardioprotective effect of a monoclonial antibody to tumor necrosis factor a in acute myocardial infarction, American Heart Journal, 1999, pp 1146–1152.

Yeh, F.L, et al; Changes in serum tumour necrosis factor–a in burned patients. Burns, vol. 23 Bi, 1, pp. 6–10, 1997.

Renzetti, L.M., et al; Ro 45–2081, a TNF receptor fusion protein, prevents inflammatory responses in the airways, Inflammation Research 46, Supplement 2, (1997), S143–S144.

Paris, M., et al; The Effect of Interleukinn–10 on Meningeal Inflammation in Experimental Bacterial Meningitis. Journal of Infectious Diseases 1997; 176:1239–1246.

Viscardi, R., et al; Inflammatory Cytokine MRNAs in Surgical Specimens of Necrotizing Enterocolitis and Normal Newborn Intestine. Pediatric Pathology of Laboratory Medicine 17:547–559, 1997.

* cited by examiner

COMPOUNDS USEFUL AS ANTI-INFLAMMATORY AGENTS

APPLICATION DATA

This application claims benefit to U.S. provisional application No. 60/291,425 filed May 16, 2001.

TECHNICAL FIELD OF THE INVENTION

This invention relates to novel compounds which possess anticytokine activity. The compounds of the invention are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

Tumor necrosis factor (TNF) and interleukin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28–38). Studies suggest that inflammatory changes mediated by cytokines may be involved in the pathogenesis of restenosis after percutaneous transluminal coronary angioplasty (PTCA) (Tashiro, H., et al., 2001 March, *Coron Artery Dis* 12(2): 107–13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, *British J. Rheum.* 35: 334–342 and Stack, W. A., et al., 1997, *Lancet* 349: 521–524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints.

Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses*, 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, Ann. Emerg. Med., 35, 26). TNFα has also been implicated in cachexia and muscle degradation, associated with HIV infection (Lahdiverta et al., 1988, Amer. J. Med., 85, 289). Obesity is associated with an increase incidence of infection, diabetes and cardiovascular disease. Abnormalities in TNFα expression have been noted for each of the above conditions (Loffreda, et al., 1998, FASEB J. 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, Med Hypotheses 47, 423). An inhibitor of TNFα production, HU-211, was shown to improve the outcome of closed brain injury in an experimental model (Shohami, et al, 1997, J Neuroimmunol. 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, Circulation, 97, 242).

TNFα levels are elevated in airways of patients with chronic obstructive pulmonary disease and it may contribute to the pathogenesis of this disease (M. A. Higham et al., 2000, Eur. Respiratory J., 15, 281). Circulating TNFα may also contribute to weight loss associated with this disease (N. Takabatake et al., 2000, Amer. J. Resp. & Crit. Care Med., 161 (4 Pt 1), 1179). Elevated TNFα levels have also been found to be associated with congestive heart failure and the level has been correlated with severity of the disease (A. M. Feldman et al., 2000, J. Amer. College of Cardiology, 35, 537). In addition, TNFα has been implicated in reperfusion injury in lung (Boijesson et al., 2000, Amer. J. Physiol., 278, L3–12), kidney (Lemay et al., 2000, Transplantation, 69, 959), and the nervous system (Mitsui et al., 1999, Brain Res., 844, 192).

TNFα is also a potent osteoclastogenic agent and is involved in bone resorption and diseases involving bone resorption (Abu-Amer et al., 2000, J. Biol. Chem., 275, 27307). It has also been found highly expressed in chondrocytes of patients with traumatic arthritis (Melchiorri et al., 2000, Arthritis and Rheumatism, 41, 2165). TNFα has also been shown to play a key role in the development of glomerulonephritis (Le Hir et al., 1998, Laboratory Investigation, 78, 1625).

The abnormal expression of inducible nitric oxide synthetase (iNOS) has been associated with hypertension in the spontaneously hypertensive rat (Chou et al., 1998, Hypertension, 31, 643). IL-1 has a role in the expression of iNOS and therefore may also have a role in the pathogenesis of hypertension (Singh et al., 1996, Amer. J. Hypertension, 9, 867).

IL-1 has also been shown to induce uveitis in rats which could be inhibited with IL-1 blockers. (Xuan et al., 1998, J. Ocular Pharmacol. and Ther., 14, 31). Cytokines including IL-1, TNF and GM-CSF have been shown to stimulate proliferation of acute myelogenous leukemia blasts (Bruserud, 1996, Leukemia Res. 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, Am J Contact Dermat. 7, 177). Data obtained from IL-1 knock out mice indicates the critical involvement in fever for this cytokine (Kluger et al., 1998, Clin Exp Pharmacol Physiol. 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, Am J Clin Nutr. 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, Molecular Medicine Today 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, Am J Rhinol. 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, Current Opinion in Hematology 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, Molecular Neurobiology 15: 307). IL-6 also plays a significant role in osteoporosis. In murine models it has been shown to effect bone resorption and to induce osteoclast activity (Ershler et al., 1997, Development and Comparative Immunol. 21: 487). Marked cytokine differences, such as IL-6 levels, exist in vivo between osteoclasts of normal bone and bone from patients with Paget's disease (Mills, et al., 1997, Calcif Tissue Int. 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, Cytokins Mol Ther. 1, 107). Several infectious diseases, such as influenza, indicate IL-6 and IFN alpha as key factors in both symptom formation and in host defense (Hayden, et al., 1998, J Clin Invest. 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, Protein Sci. 6, 929). Compounds that interfered with the production of cytokines including IL-6, and TNF were effective in blocking a passive cutaneous anaphylaxis in mice (Scholz et al., 1998, J. Med. Chem., 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol*. 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma*. 19, 173). The development of insulin-dependent diabetes (Type 1) can be correlated with the accumulation in pancreatic islet cells of T-cells producing IFN γ (Ablumunits, et al., 1998, *J Autoimmun*. 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol*. 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol*. 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol*. 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg*. 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med*. 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol*. 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al., 1996, *J Bone Miner Res*. 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon*. 43, 277). IFN γ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther*. 10 *Suppl* 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNF-alpha. The specific inhibitors disclosed are structurally distinct from the novel compounds disclosed in the present application disclosed hereinbelow. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalopathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas and their use in treating cytokine diseases and proteolytic enzyme mediated disease. WO 00/41698 discloses aryl ureas said to be useful in treating p38 MAP kinase diseases.

U.S. Pat. No. 5,162,360 discloses N-substituted aryl-N'-heterocyclic substituted urea compounds which are described as being useful for treating hypercholesterolemia and atheroclerosis.

The work cited above supports the principle that inhibition of cytokine production will be beneficial in the treatment of various disease states. Some protein therapeutics are in late development or have been approved for use in particular diseases. Protein therapeutics are costly to produce and have bioavailability and stability problems. Therefore a need exists for new small molecule inhibitors of cytokine production with optimized efficacy, pharmacokinetic and safety profiles.

BRIEF SUMMARY OF THE INVENTION

The work cited above supports the principle that inhibition of cytokine production will be beneficial in the treatment of various disease states.

It is therefore an object of the invention to provide novel compounds which inhibit the release of inflammatory cytokines such as interleukin-1 and tumor necrosis factor.

It is a further object of the invention to provide methods for treating diseases and pathological conditions involving inflammation such as chronic inflammatory disease, using the novel compounds of the invention.

It is yet a further object of the invention to provide processes of preparation of the above-mentioned novel compounds.

DETAILED DECRIPTION OF THE INVENTION

In a first embodiment, the invention provide the following compounds:

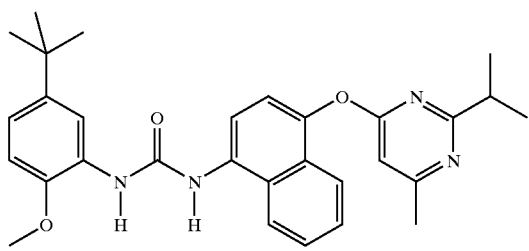

1-(5-tert-Butyl-2-methoxy-phenyl)-3-[4-(2-isopropyl-6-methyl-pyrimidin-4-yloxy)-naphthalen-1-yl]-urea;

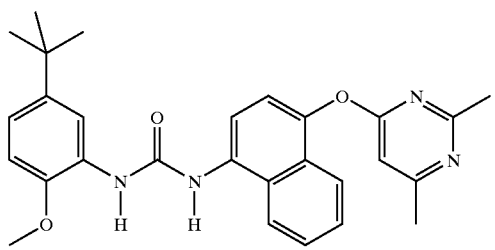

1-(5-tert-Butyl-2-methoxy-phenyl)-3-[4-(2,6-dimethyl-pyrimidin-4-yloxy)-naphthalen-1-yl]-urea;

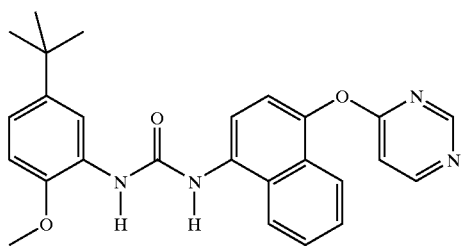

1-(5-tert-Butyl-2-methoxy-phenyl)-3-[4-(pyrimidin-4-yloxy)-naphthalen-1-yl]-urea;

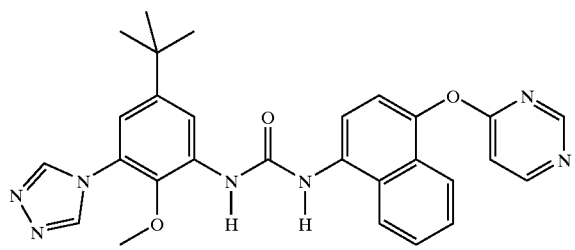

1-(5-tert-Butyl-2-methoxy-3-[1,2,4]triazol-4-yl-phenyl)-3-[4-(pyrimidin-4-yloxy)-naphthalen-1-yl]-urea;

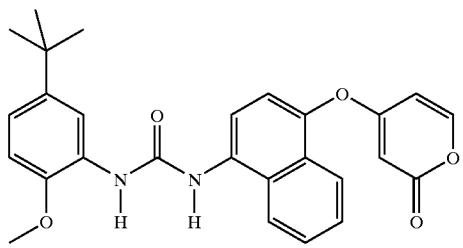

1-(5-tert-Butyl-2-methoxy-phenyl)-3-[4-(2-oxo-2H-pyran-4-yloxy)-naphthalen-1-yl]-urea;

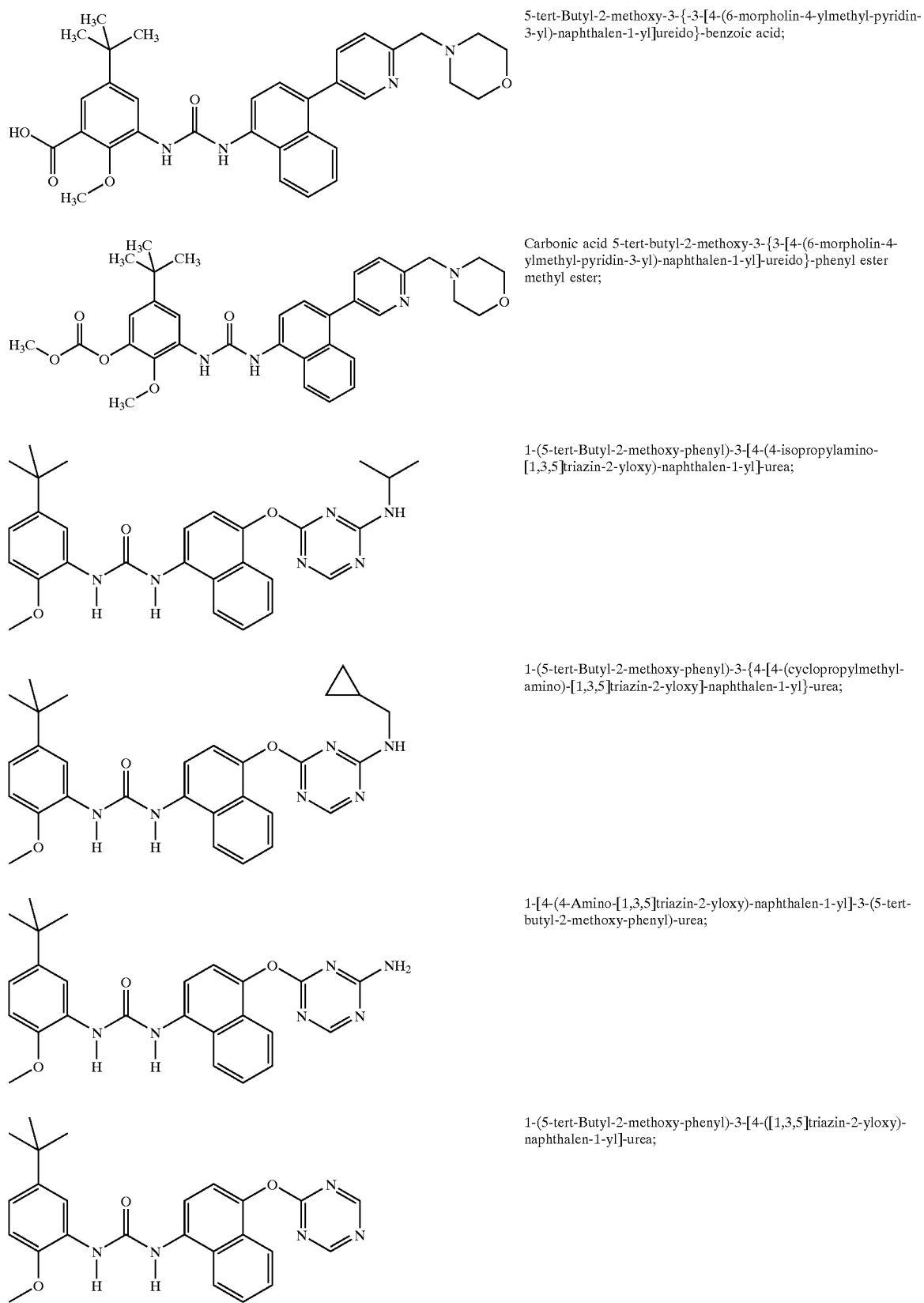

5-tert-Butyl-2-methoxy-3-{-3-[4-(6-morpholin-4-ylmethyl-pyridin-3-yl)-naphthalen-1-yl]ureido}-benzoic acid;

Carbonic acid 5-tert-butyl-2-methoxy-3-{3-[4-(6-morpholin-4-ylmethyl-pyridin-3-yl)-naphthalen-1-yl]-ureido}-phenyl ester methyl ester;

1-(5-tert-Butyl-2-methoxy-phenyl)-3-[4-(4-isopropylamino-[1,3,5]triazin-2-yloxy)-naphthalen-1-yl]-urea;

1-(5-tert-Butyl-2-methoxy-phenyl)-3-{4-[4-(cyclopropylmethyl-amino)-[1,3,5]triazin-2-yloxy]-naphthalen-1-yl}-urea;

1-[4-(4-Amino-[1,3,5]triazin-2-yloxy)-naphthalen-1-yl]-3-(5-tert-butyl-2-methoxy-phenyl)-urea;

1-(5-tert-Butyl-2-methoxy-phenyl)-3-[4-([1,3,5]triazin-2-yloxy)-naphthalen-1-yl]-urea;

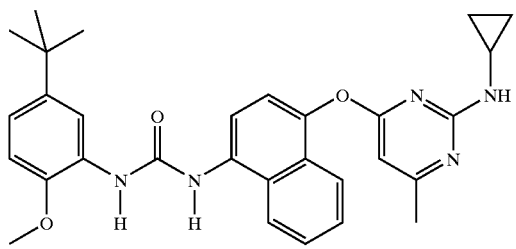

1-(5-tert-Butyl-2-methoxy-phenyl)-3-[4-(2-cyclopropylamino-6-methyl-pyrimidin-4-yloxy)-naphthalen-1-yl]-urea;

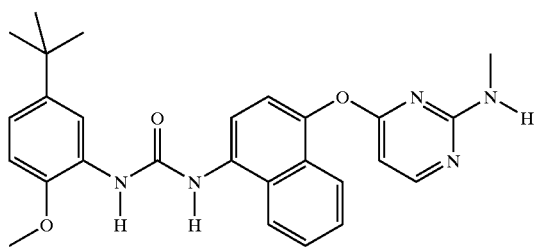

1-(5-tert-Butyl-2-methoxy-phenyl)-3-[4-(2-methylamino-pyrimidin-4-yloxy)-naphthalen-1-yl]-urea;

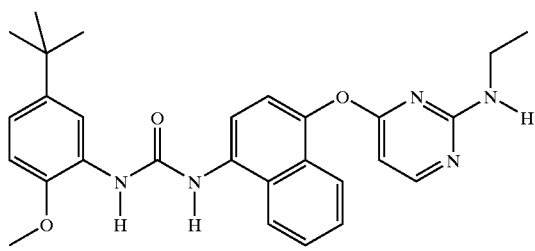

1-(5-tert-Butyl-2-methoxy-phenyl)-3-[4-(2-ethylamino-pyrimidin-4-yloxy)-naphthalen-1-yl]-urea;

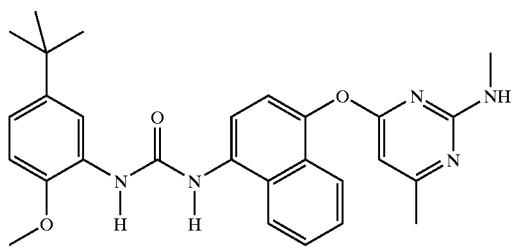

1-(5-tert-Butyl-2-methoxy-phenyl)-3-[4-(6-methyl-2-methylamino-pyrimidin-4-yloxy)-naphthalen-1-yl]-urea;

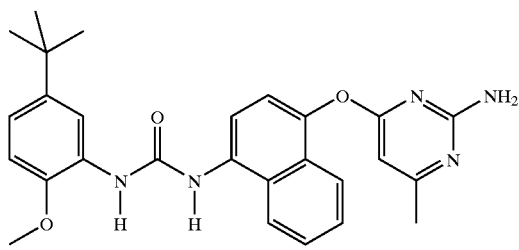

1-[4-(2-Amino-6-methyl-pyrimidin-4-yloxy)-naphthalen-1-yl]-3-(5-tert-butyl-2-methoxy-phenyl)-urea;

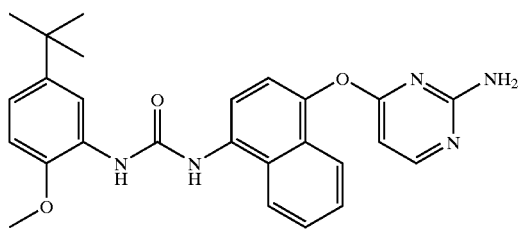

1-[4-(2-Amino-pyrimidin-4-yloxy)-naphthalen-1-yl]-3-(5-tert-butyl-2-methoxy-phenyl)-urea;

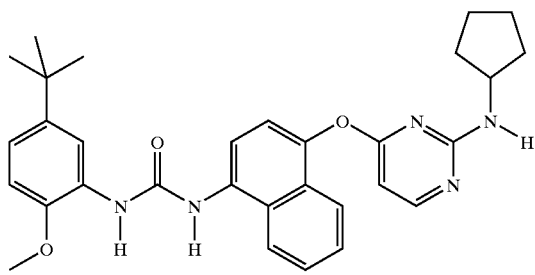
1-(5-tert-Butyl-2-methoxy-phenyl)-3-[4-(2-cyclopentylamino-pyrimidin-4-yloxy)-naphthalen-1-yl]urea;

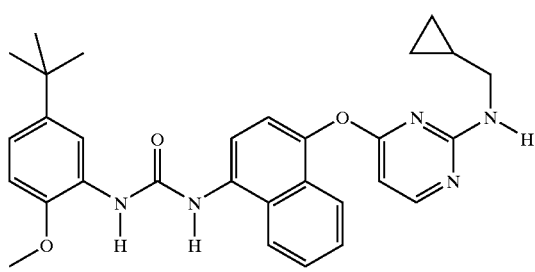
1-(5-tert-Butyl-2-methoxy-phenyl)-3-{4-[2-(cyclopropylmethyl-amino)-pyrimidin-4-yloxy]-naphthalen-1-yl}-urea;

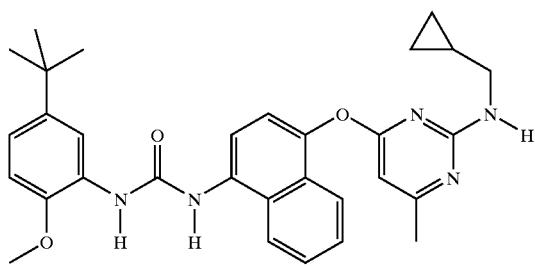
1-(5-tert-Butyl-2-methoxy-phenyl)-3-{4-[2-(cyclopropylmethyl-amino)-6-methyl-pyrimidin-4-yloxy]naphthalen-1-yl}-urea;

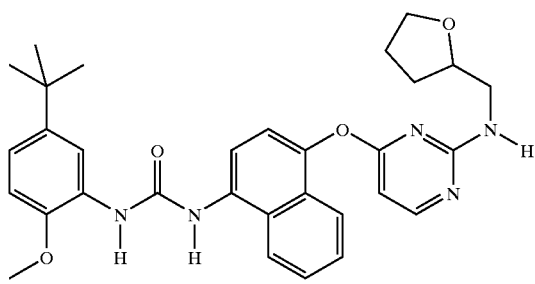
1-(5-tert-Butyl-2-methoxy-phenyl)-3-(4-{2-[(tetrahydro-furan-2-ylmethyl)-amino]-pyrimidin-4-yloxy}-naphthalen-1-yl)-urea;

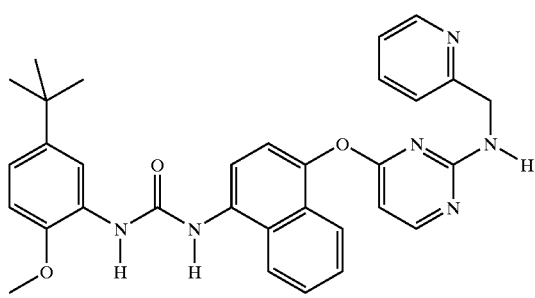
1-(5-tert-Butyl-2-methoxy-phenyl)-3-(4-{2-[(pyridin-2-ylmethyl)-amino]-pyrimidin-4-yloxy}-naphthalen-1-yl)-urea;

-continued

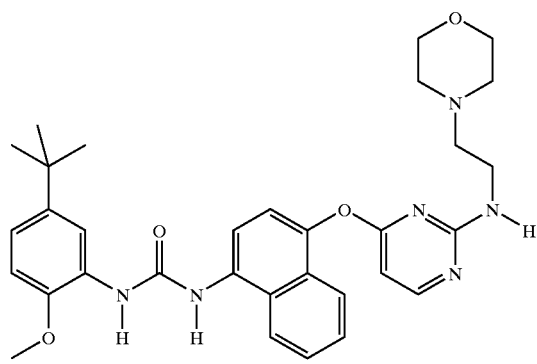 1-(5-tert-Butyl-2-methoxy-phenyl)-3-{4-[2-(2-morpholin-4-yl-ethylamino)-pyrimidin-4-yloxy]-naphthalen-1-yl}-urea;

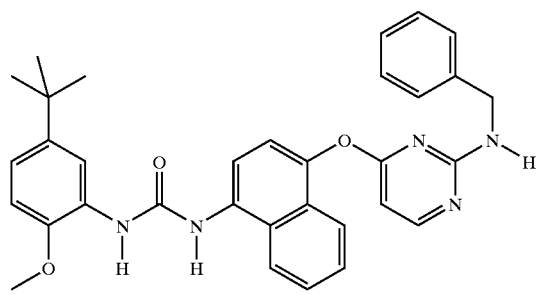 1-[4-(2-Benzylamino-pyrimidin-4-yloxy)-naphthalen-1-yl]-3-(5-tert-butyl-2-methoxy-phenyl)-urea;

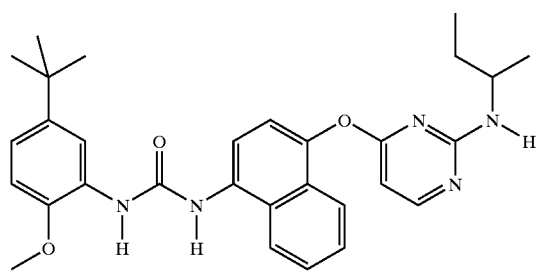 1-[4-(2-sec-Butylamino-pyrimidin-4-yloxy)-naphthalen-1-yl]-3-(5-tert-butyl-2-methoxy-phenyl)-urea;

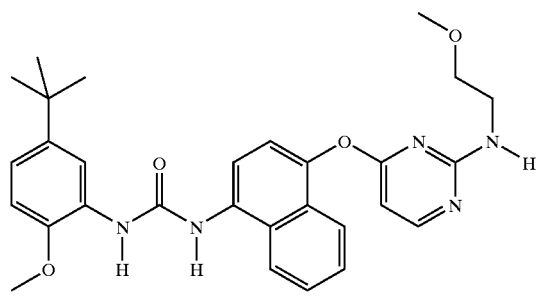 1-(5-tert-Butyl-2-methoxy-phenyl)-3-{4-[2-(2-methoxy-ethylamino)-pyrimidin-4-yloxy]-naphthalen-1-yl}-urea;

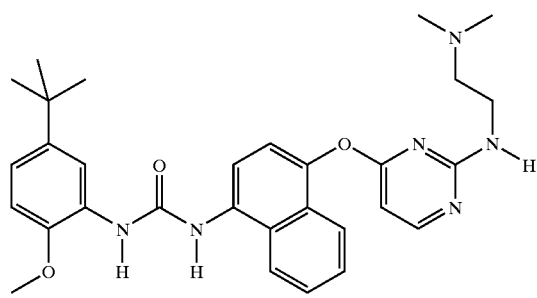 1-(5-tert-Butyl-2-methoxy-phenyl)-3-{4-[2-(2-dimethylamino-ethylamino)-pyrimidin-4-yloxy]-naphthalen-1-yl}-urea;

-continued

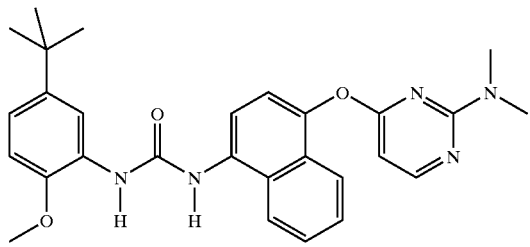
1-(5-tert-Butyl-2-methoxy-phenyl)-3-[4-(2-dimethylamino-pyrimidin-4-yloxy)-naphthalen-1-yl]-urea;

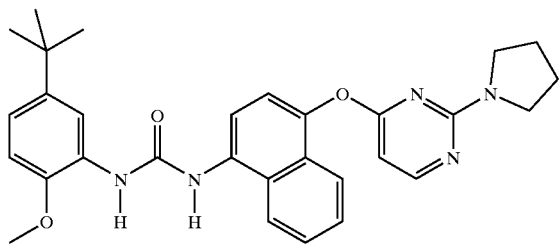
1-(5-tert-Butyl-2-methoxy-phenyl)-3-[4-(2-pyrrolidin-1-yl-pyrimidin-4-yloxy)-naphthalen-1-yl]-urea;

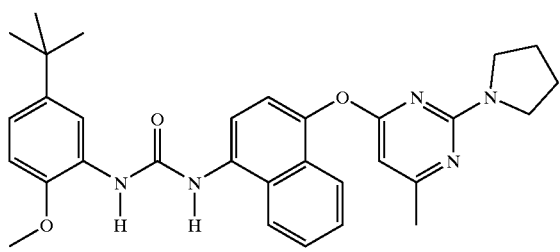
1-(5-tert-Butyl-2-methoxy-phenyl)-3-[4-(6-methyl-2-pyrrolidin-1-yl-pyrimidin-4-yloxy)-naphthalen-1-yl]-urea;

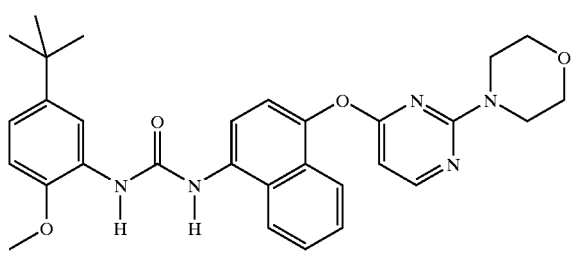
1-(5-tert-Butyl-2-methoxy-phenyl)-3-[4-(2-morpholin-4-yl-pyrimidin-4-yloxy)-naphthalen-1-yl]-urea;

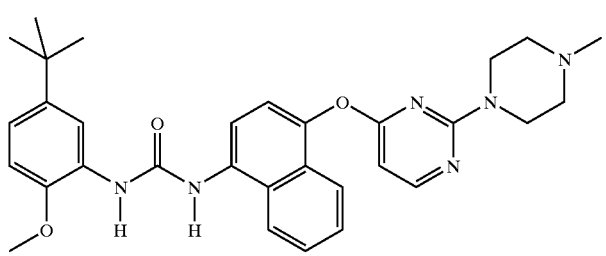
1-(5-tert-Butyl-2-methoxy-phenyl)-3-{4-[2-(4-methyl-piperazin-1-yl)-pyrimidin-4-yloxy]-naphthalen-1-yl}-urea;

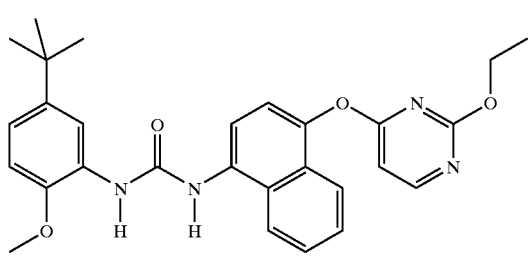
1-(5-tert-Butyl-2-methoxy-phenyl)-3-[4-(2-ethoxy-pyrimidin-4-yloxy)-naphthalen-1-yl]-urea;

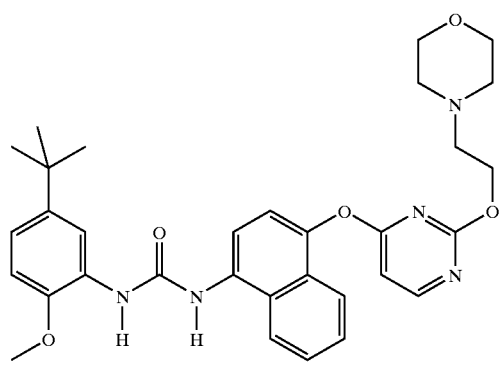

1-(5-tert-Butyl-2-methoxy-phenyl)-3-{4-[2-(2-morpholin-4-yl-ethoxy)-pyrimidin-4-yloxy]-naphthalen-1-yl}urea;

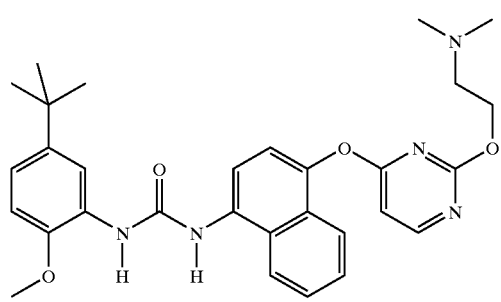

1-(5-tert-Butyl-2-methoxy-phenyl)-3-{4-[2-(2-dimethylamino-ethoxy)-pyrimidin-4-yloxy]-naphthalen-1-yl}-urea;

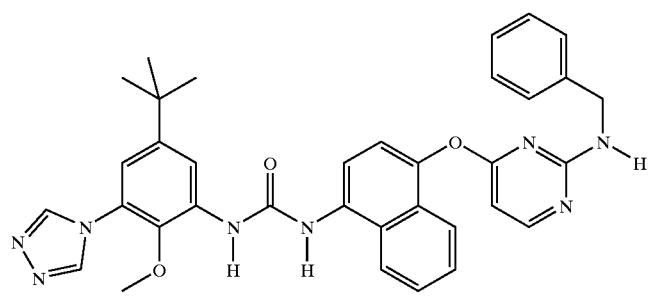

1-[4-(2-Benzylamino-pyrimidin-4-yloxy)-naphthalen-1-yl]-3-(5-tert-butyl-2-methoxy-3-[1,2,4]triazol-4-yl-phenyl)-urea;

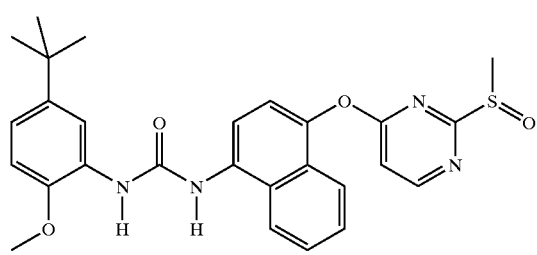

1-(5-tert-Butyl-2-methoxy-phenyl)-3-[4-(2-methanesulfinyl-pyrimidin-4-yloxy)-naphthalen-1-yl]-urea;

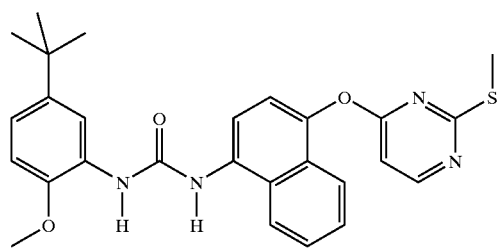

1-(5-tert-Butyl-2-methoxy-phenyl)-3-[4-(2-methylsulfanyl-pyrimidin-4-yloxy)-naphthalen-1-yl]-urea;

-continued

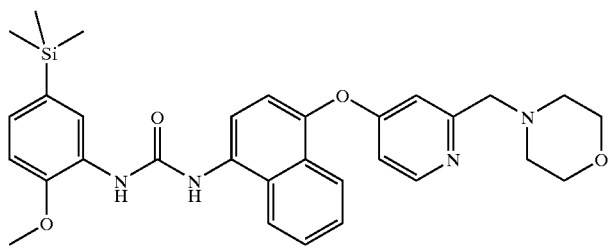

1-(2-Methoxy-5-trimethylsilanyl-phenyl)-3-[4-(6-morpholin-4-ylmethyl-pyridin-3-yl)-naphthalen-1-yl]-urea;

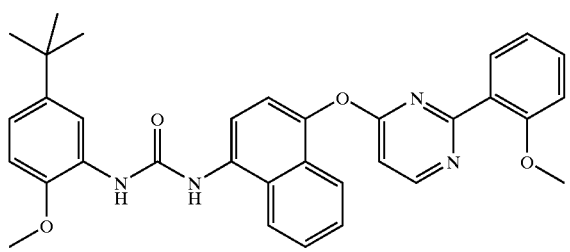

1-(5-tert-Butyl-2-methoxy-phenyl)-3-{4-[2-(2-methoxy-phenyl)-pyrimidin-4-yloxy]-naphthalen-1-yl}-urea;

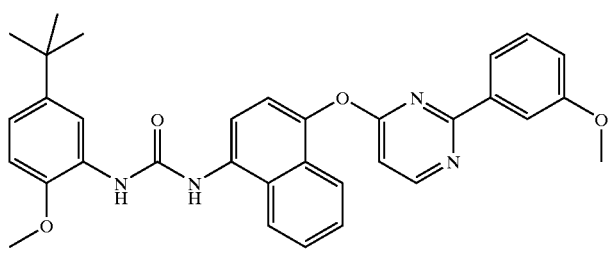

1-(5-tert-Butyl-2-methoxy-phenyl)-3-{4-[2-(3-methoxy-phenyl)-pyrimidin-4-yloxy]-naphthalen-1-yl}-urea;

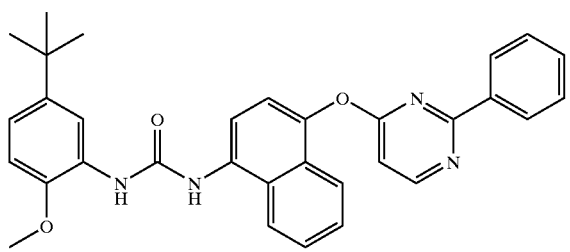

1-(5-tert-Butyl-2-methoxy-phenyl)-3-[4-(2-phenyl-pyrimidin-4-yloxy)-naphthalen-1-yl]-urea;

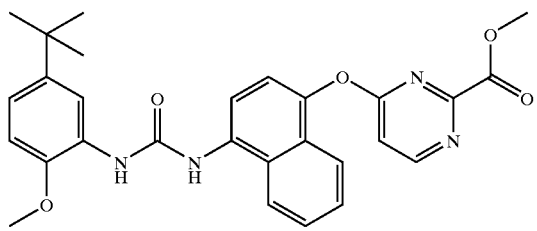

4-{4-[3-(5-tert-Butyl-2-methoxy-phenyl)-ureido]-naphthalen-1-yloxy}-pyrimidine-2-carboxylic acid methyl ester;

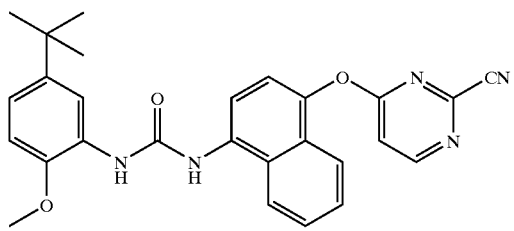

1-(5-tert-Butyl-2-methoxy-phenyl)-3-[4-(2-cyano-pyrimidin-4-yloxy)-naphthalen-1-yl]-urea;

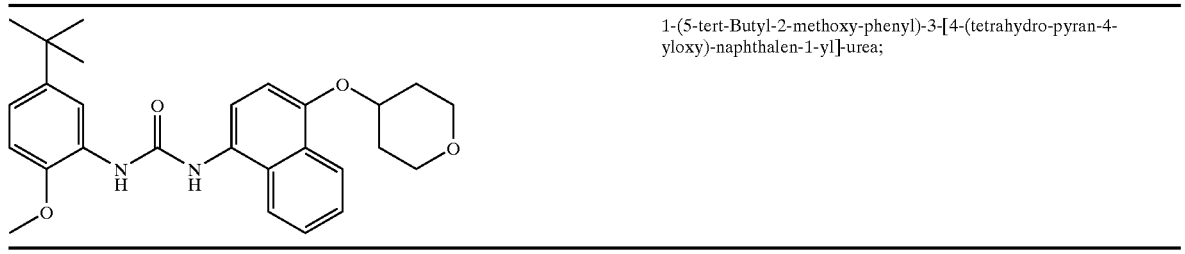

1-(5-tert-Butyl-2-methoxy-phenyl)-3-[4-(tetrahydro-pyran-4-yloxy)-naphthalen-1-yl]-urea;

or the pharmaceutically acceptable derivatives thereof.

In a second embodiment, the invention provides the following compounds:

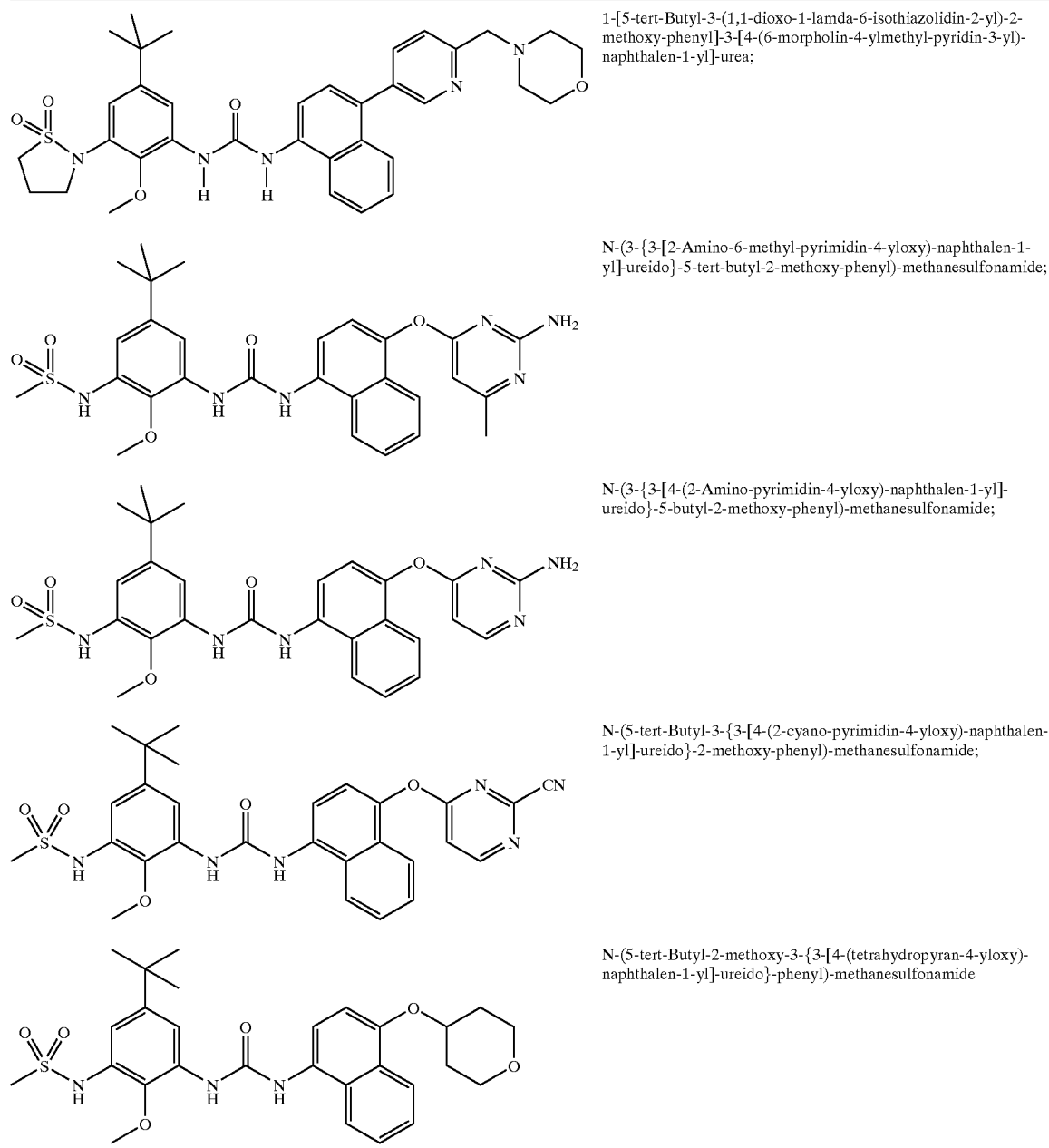

1-[5-tert-Butyl-3-(1,1-dioxo-1-lamda-6-isothiazolidin-2-yl)-2-methoxy-phenyl]-3-[4-(6-morpholin-4-ylmethyl-pyridin-3-yl)-naphthalen-1-yl]-urea;

N-(3-{3-[2-Amino-6-methyl-pyrimidin-4-yloxy)-naphthalen-1-yl]-ureido}-5-tert-butyl-2-methoxy-phenyl)-methanesulfonamide;

N-(3-{3-[4-(2-Amino-pyrimidin-4-yloxy)-naphthalen-1-yl]-ureido}-5-butyl-2-methoxy-phenyl)-methanesulfonamide;

N-(5-tert-Butyl-3-{3-[4-(2-cyano-pyrimidin-4-yloxy)-naphthalen-1-yl]-ureido}-2-methoxy-phenyl)-methanesulfonamide;

N-(5-tert-Butyl-2-methoxy-3-{3-[4-(tetrahydropyran-4-yloxy)-naphthalen-1-yl]-ureido}-phenyl)-methanesulfonamide

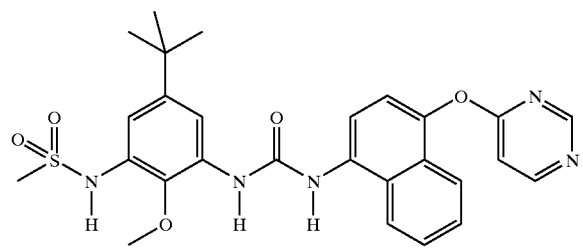

N-(5-tert-Butyl-2-methoxy-3-{3-[4-(pyrimidin-4-yloxy)-naphthalen-1-yl]-ureido}-phenyl)-methanesulfonamide;

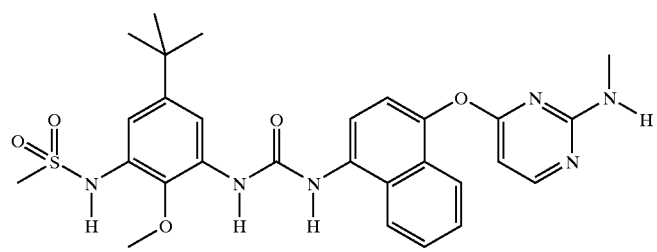

N-(5-tert-Butyl-2-methoxy-3-{3-[4-(2-methylamino-pyrimidin-4-yloxy)-naphthalen-1-yl]-ureido}-phenyl)-methanesulfonamide;

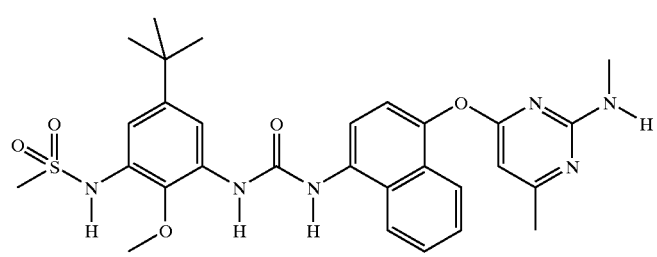

N-(5-tert-Butyl-2-methoxy-3-{3-[4-(6-methyl-2-methylamino-pyrimidin-4-yloxy)-naphthalen-1-yl]-ureido}-phenyl)-methanesulfonamide;

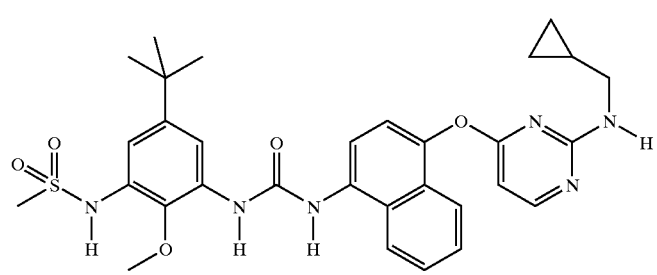

N-[5-tert-Butyl-3-(3-{4-[2-(cyclopropulmethyl-amino)-pyrimidin-4-yloxy]-naphthalen-1-yl}-ureido)-2-methoxy-phenyl]-methanesulfonamide;

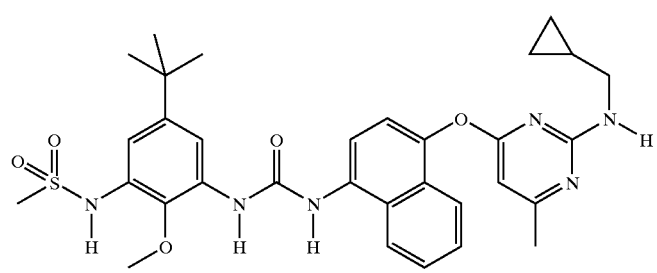

N-[5-tert-Butyl-3-(3-{4-[2-(cyclopropylmethyl-amino)-6-methyl-pyrimidin-4-yloxy]-naphthalen-1-yl}-ureido)-2-methoxy-phenyl]-methanesulfonamide;

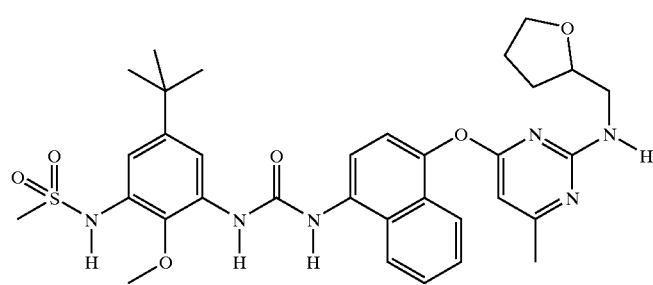

N-{5-tert-Butyl-2-methoxy-3-[3-(4-{2-[(tetrahydro-furan-2-ylmethyl)-amino]-pyrimidin-4-yloxy}-naphthalen-1-yl)-ureido]-phenyl}-methanesulfonamide;

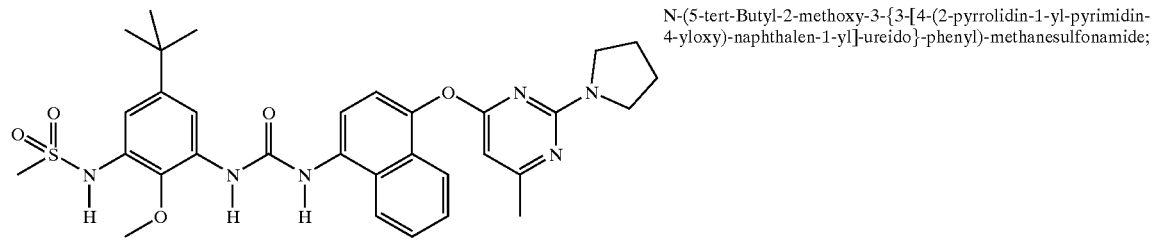

N-(5-tert-Butyl-2-methoxy-3-{3-[4-(2-pyrrolidin-1-yl-pyrimidin-4-yloxy)-naphthalen-1-yl]-ureido}-phenyl)-methanesulfonamide;

or the pharmaceutically acceptable derivatives thereof.

In a third embodiment, the invention provides the following compounds:

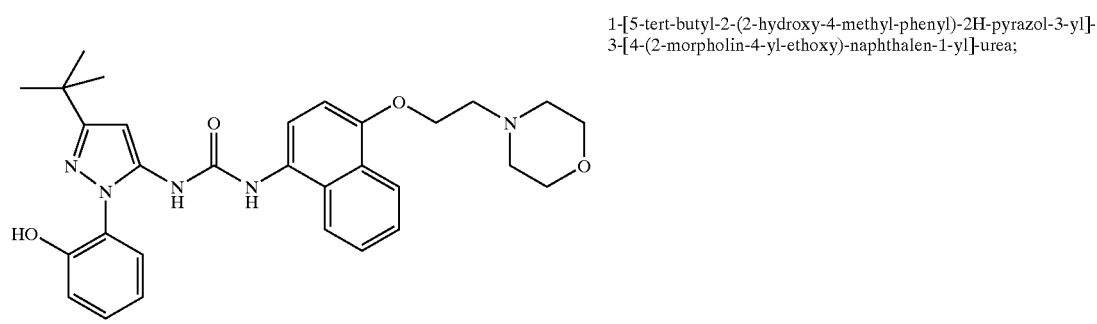

1-[5-tert-butyl-2-(2-hydroxy-4-methyl-phenyl)-2H-pyrazol-3-yl]-3-[4-(2-morpholin-4-yl-ethoxy)-naphthalen-1-yl]-urea;

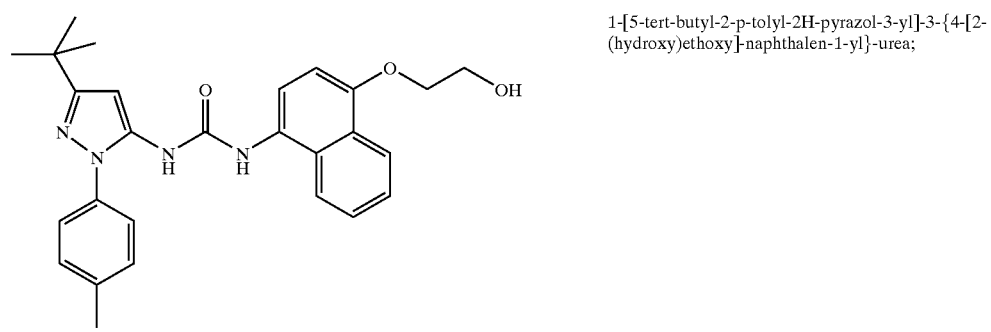

1-[5-tert-butyl-2-p-tolyl-2H-pyrazol-3-yl]-3-{4-[2-(hydroxy)ethoxy]-naphthalen-1-yl}-urea;

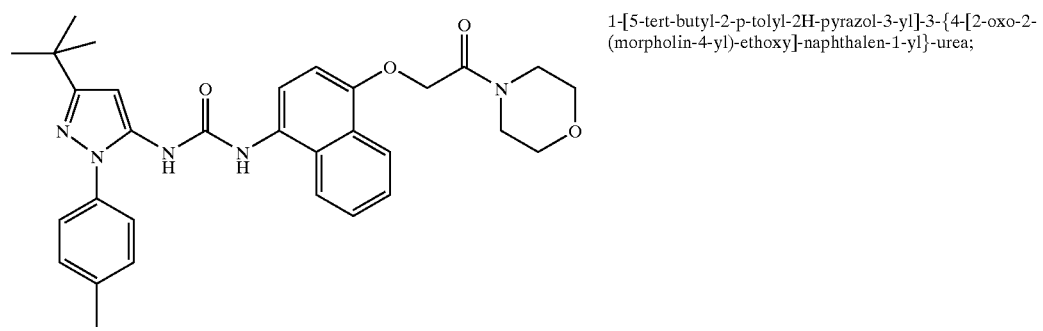

1-[5-tert-butyl-2-p-tolyl-2H-pyrazol-3-yl]-3-{4-[2-oxo-2-(morpholin-4-yl)-ethoxy]-naphthalen-1-yl}-urea;

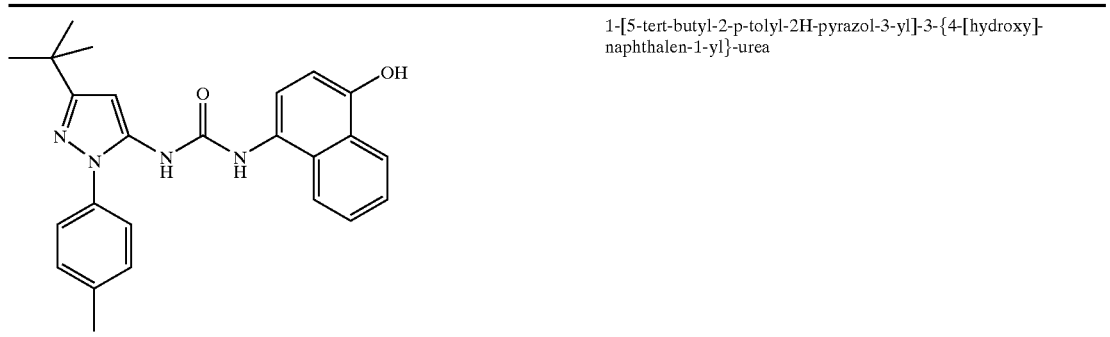

1-[5-tert-butyl-2-p-tolyl-2H-pyrazol-3-yl]-3-{4-[hydroxy]-naphthalen-1-yl}-urea or the pharmaceutically acceptable derivatives thereof.

In a fourth embodiment, the invention provides the following compounds which can be made be the procedures illustrated in the General Synthetic Methods and Experimental section provided herein below:

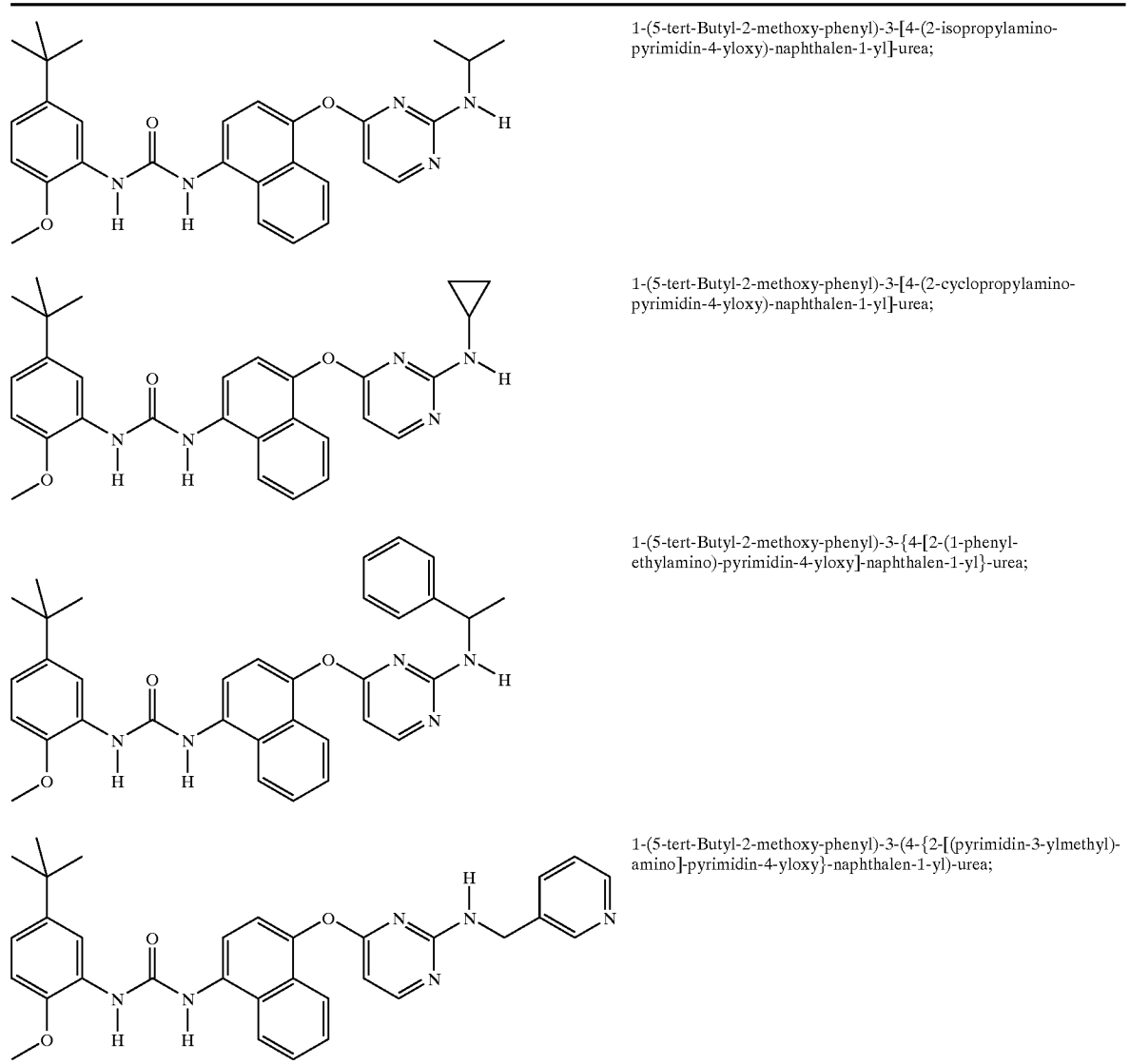

1-(5-tert-Butyl-2-methoxy-phenyl)-3-[4-(2-isopropylamino-pyrimidin-4-yloxy)-naphthalen-1-yl]-urea;

1-(5-tert-Butyl-2-methoxy-phenyl)-3-[4-(2-cyclopropylamino-pyrimidin-4-yloxy)-naphthalen-1-yl]-urea;

1-(5-tert-Butyl-2-methoxy-phenyl)-3-{4-[2-(1-phenyl-ethylamino)-pyrimidin-4-yloxy]-naphthalen-1-yl}-urea;

1-(5-tert-Butyl-2-methoxy-phenyl)-3-(4-{2-[(pyrimidin-3-ylmethyl)-amino]-pyrimidin-4-yloxy}-naphthalen-1-yl)-urea;

-continued

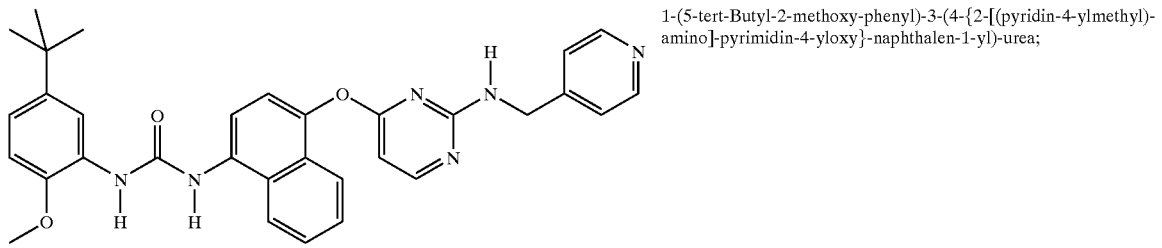

1-(5-tert-Butyl-2-methoxy-phenyl)-3-(4-{2-[(pyridin-4-ylmethyl)-amino]-pyrimidin-4-yloxy}-naphthalen-1-yl)-urea;

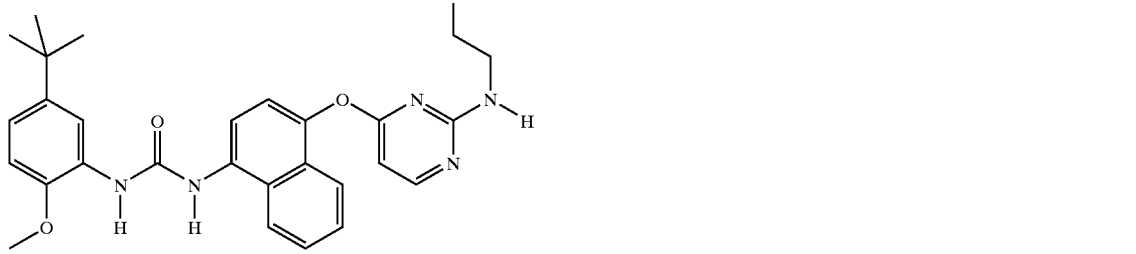

1-(5-tert-Butyl-2-methoxy-phenyl)-3-(4-{2-[2-(4-methyl-piperazin-1-yl)-ethylamino]-pyrimidin-4-yloxy}-naphthalen-1-yl)-urea;

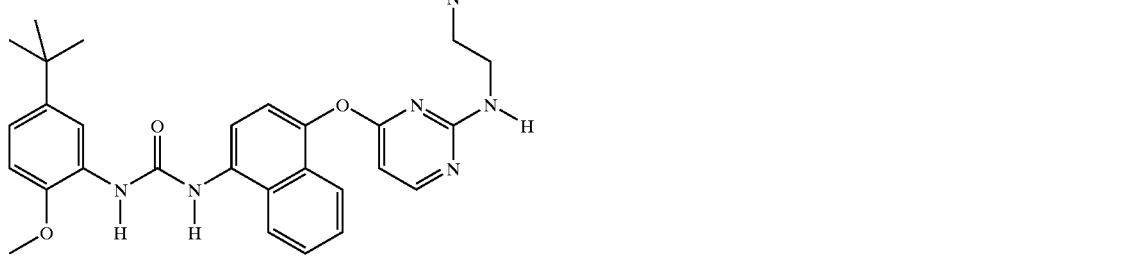

1-(5-tert-Butyl-2-methoxy-phenyl)-3-{4-[2-(2-pyrrolidin-1-yl-ethylamino)-pyrimidin-4-yloxy]-naphthalen-1-yl}-urea;

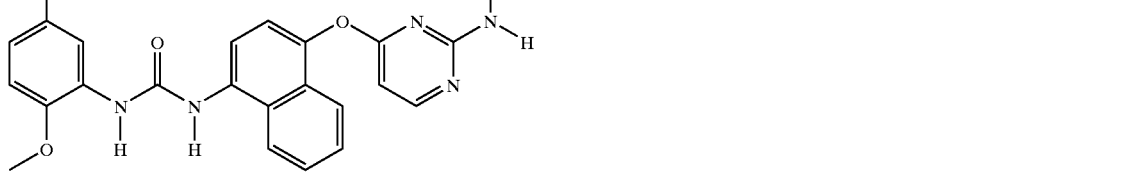

1-(5-tert-Butyl-2-methoxy-phenyl)-3-{4-[2-(2-oxo-tetrahydro-furan-3-ylamino)-pyrimidin-4-yloxy]-naphthalen-1-yl}-urea;

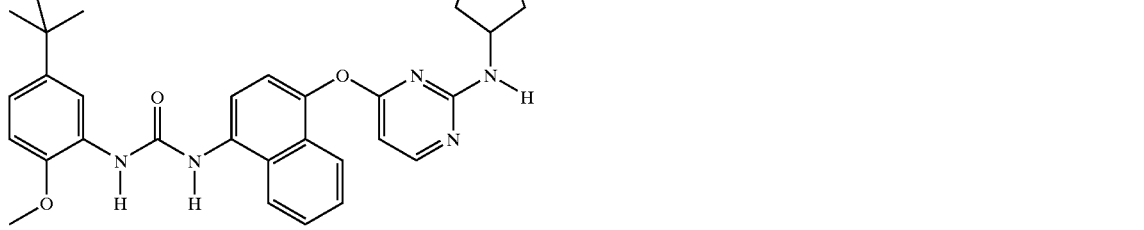

1-(5-tert-Butyl-2-methoxy-phenyl)-3-{4-[2-(tetrahydro-furan-3-ylamino)-pyrimidin-4-yloxy]-naphthalen-1-yl}-urea;

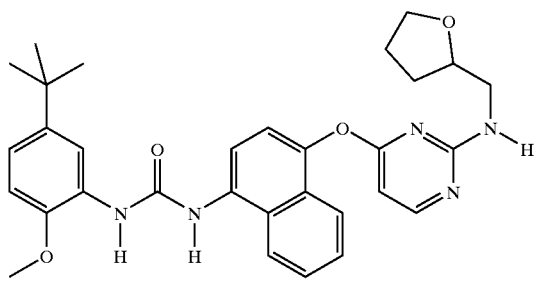

1-(5-tert-Butyl-2-methoxy-phenyl)-3-(4-{6-methyl-2-[(tetrahydro-furan-2-ylmethyl)-amino]-pyrimidin-4-yloxy}-naphthalen-1-yl)-urea;

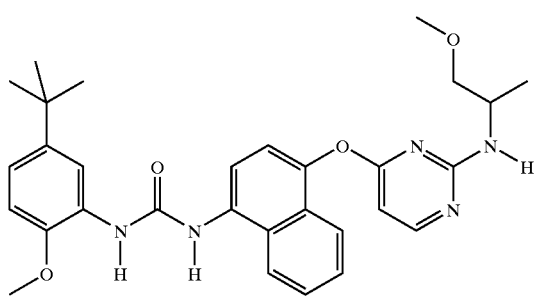

1-(5-tert-Butyl-2-methoxy-phenyl)-3-{4-[2-(2-methoxy-1-methyl-ethylamino)-pyrimidin-4-yloxy]-naphthalen-1-yl}-urea;

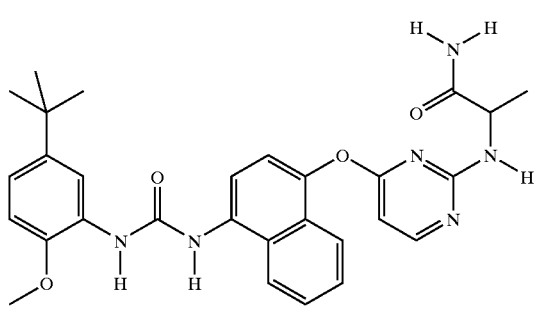

2-(4-{4-[3-(5-tert-Butyl-2-methoxy-phenyl)-ureido]-naphthalen-1-yloxy}-pyrimidin-2-ylamino)-propionamide;

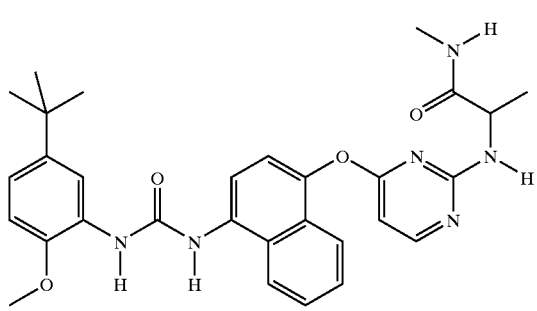

2-(4-{4-[3-(5-tert-Butyl-2-methoxy-phenyl)-ureido]-naphthalen-1-yloxy}-pyrimidin-2-ylamino)-N-methyl-propionamide;

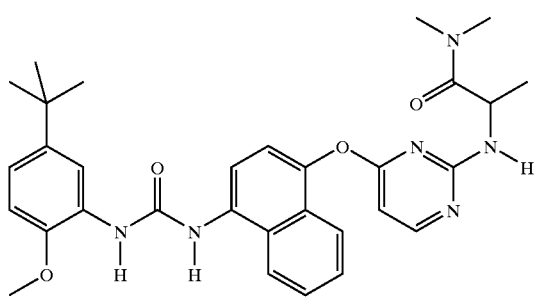

2-(4-{4-[3-(5-tert-Butyl-2-methoxy-phenyl)-ureido]-naphthalen-1-yloxy}-pyrimidin-2-ylamino)-N,N-dimethyl-propionamide;

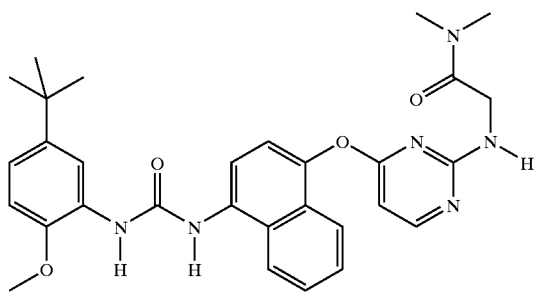

2-(4-{4-[3-(5-tert-Butyl-2-methoxy-phenyl)-ureido]-naphthalen-1-yloxy}-pyrimidin-2-ylamino)-N,N-dimethyl-acetamide

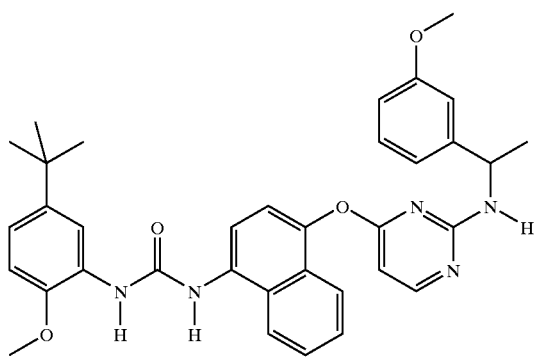

1-(5-tert-Butyl-2-methoxy-phenyl)-3-(4-{2-[1-(3-methoxy-phenyl)-ethylamino]-pyrimidin-4-yloxy}-naphthalen-1-yl)-urea;

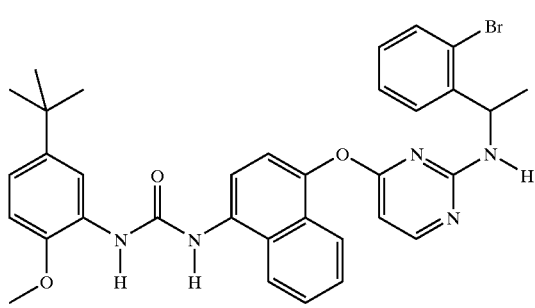

1-(4-{2-[1-(2-Bromo-phenyl)-ethylamino]-pyrimidin-4-yloxy}-naphthalen-1-yl)-3-(5-tert-butyl-2-methoxy-phenyl)-urea;

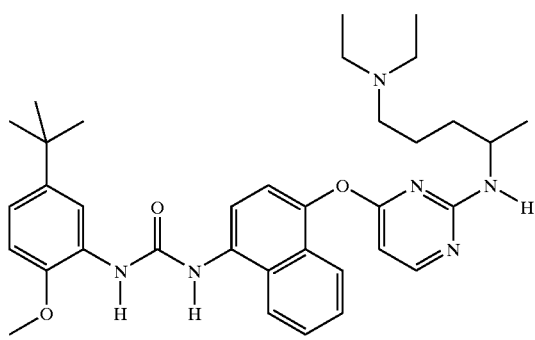

1-(5-tert-Butyl-2-methoxy-phenyl)-3-{4-[2-(4-diethylamino-1-methyl-butylamino)-pyrimidin-4-yloxy]-naphthalen-1-yl}-urea;

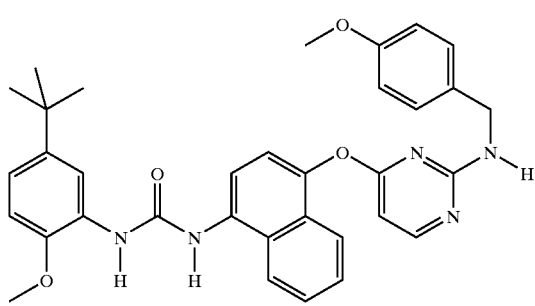

1-(5-tert-Butyl-2-methoxy-phenyl)-3-{4-[2-(4-methoxy-benzylamino)-pyrimidin-4-yloxy]-naphthalen-1-yl}-urea;

-continued

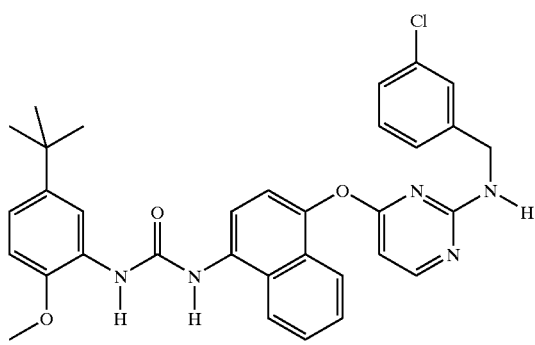
1-(5-tert-Butyl-2-methoxy-phenyl)-3-{4-[2-(3-chloro-benzylamino)-pyrimidin-4-yloxy]-naphthalen-1-yl}-urea;

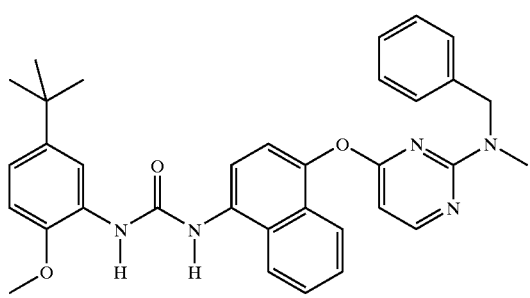
1-{4-[2-(Benyl-methyl-amino)-pyrimidin-4-yloxy]-naphthalen-1-yl}-3-(5-tert-butyl-2-methoxy-phenyl)-urea;

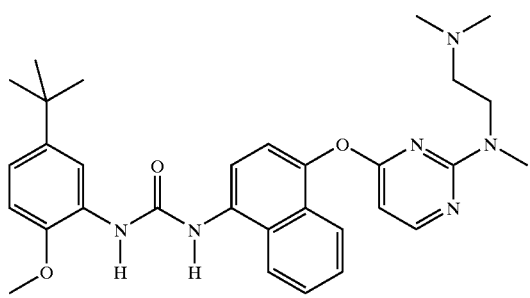
1-(5-tert-Butyl-2-methoxy-phenyl)-3-(4-{2-[(2-dimethtlamino-ethyl)-methyl-amino]-pyrimidin-4-yloxy}-naphthalen-1-yl)-urea;

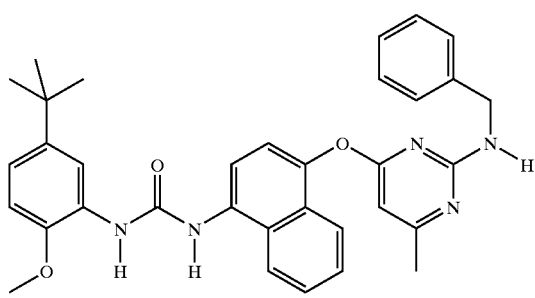
1-[4-(2-Benzylamino-6-methyl-pyrimidin-4-yloxy)-naphthalen-1-yl]-3-(5-tert-butyl-2-methoxy-phenyl)-urea;

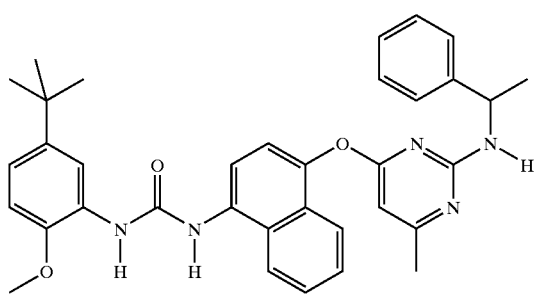
1-(5-tert-Butyl-2-methoxy-phenyl)-3-{4-[6-methyl-2-(1-phenyl-ethylamino)-pyrimidin-4-yloxy]-naphthalen-1-yl}-urea;

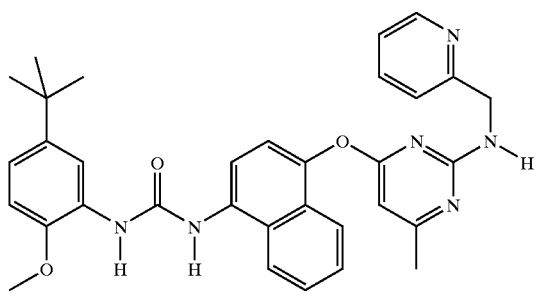 1-(5-tert-Butyl-2-methoxy-phenyl)-3-(4-{6-methyl-2-[(pyridin-2-ylmethyl)-amino]-pyrimidin-4-yloxy}-naphthalen-1-yl)-urea;

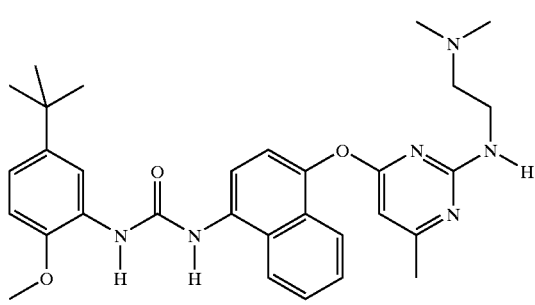 1-(5-tert-Butyl-2-methoxy-phenyl)-3-{4-[2-(2-dimethylamino-ethylamino)-6-methyl-pyrimidin-4-yloxy]-naphthalen-1-yl}-urea;

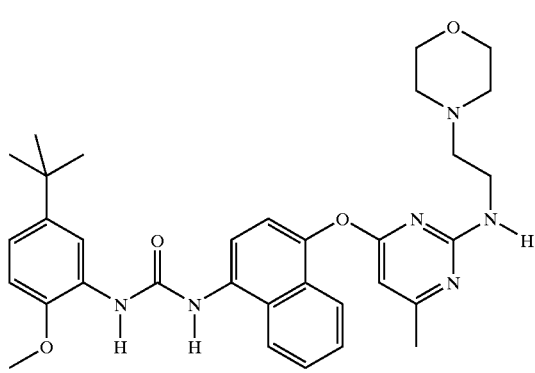 1-(5-tert-Butyl-2-methoxy-phenyl)-3-{4-[6-methyl-2-(2-morpholin-4-yl-ethylamino)-pyrimidin-4-yloxy]-naphthalen-1-yl}-urea;

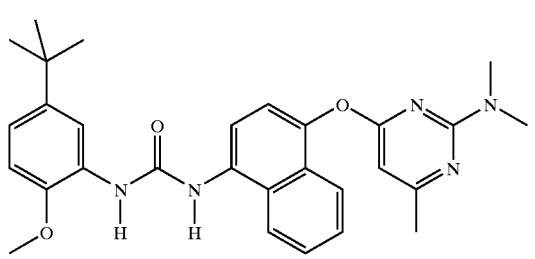 1-(5-tert-Butyl-2-methoxy-phenyl)-3-[4-(2-dimethylamino-6-methyl-pyrimidin-4-yloxy)-naphthalen-1-yl]-urea;

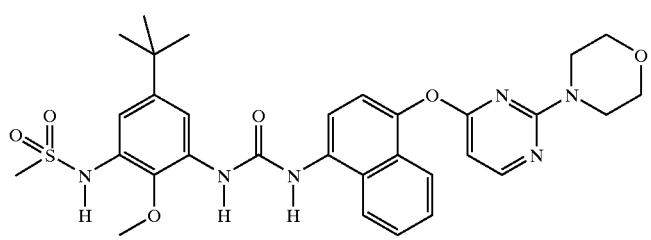 N-(5-tert-Butyl-2-methyl-3-{3-[4-(2-morpholin-4-yl-pyrimidin-4-yloxy)-naphthalen-1-yl]-ureido}-phenyl)-methanesulfonamide;

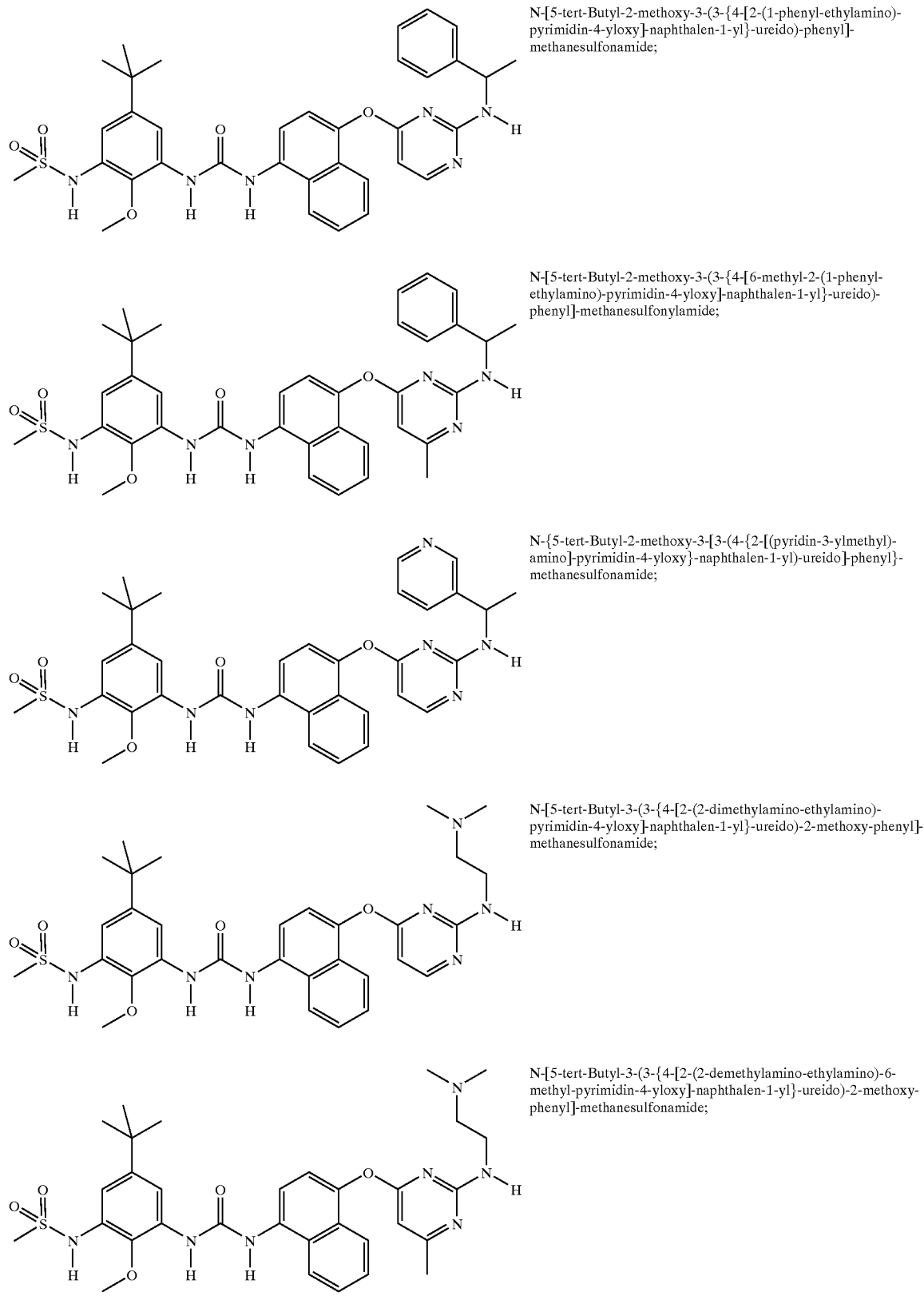

N-[5-tert-Butyl-2-methoxy-3-(3-{4-[2-(1-phenyl-ethylamino)-pyrimidin-4-yloxy]-naphthalen-1-yl}-ureido)-phenyl]-methanesulfonamide;

N-[5-tert-Butyl-2-methoxy-3-(3-{4-[6-methyl-2-(1-phenyl-ethylamino)-pyrimidin-4-yloxy]-naphthalen-1-yl}-ureido)-phenyl]-methanesulfonylamide;

N-{5-tert-Butyl-2-methoxy-3-[3-(4-{2-[(pyridin-3-ylmethyl)-amino]-pyrimidin-4-yloxy}-naphthalen-1-yl)-ureido]-phenyl}-methanesulfonamide;

N-[5-tert-Butyl-3-(3-{4-[2-(2-dimethylamino-ethylamino)-pyrimidin-4-yloxy]-naphthalen-1-yl}-ureido)-2-methoxy-phenyl]-methanesulfonamide;

N-[5-tert-Butyl-3-(3-{4-[2-(2-demethylamino-ethylamino)-6-methyl-pyrimidin-4-yloxy]-naphthalen-1-yl}-ureido)-2-methoxy-phenyl]-methanesulfonamide;

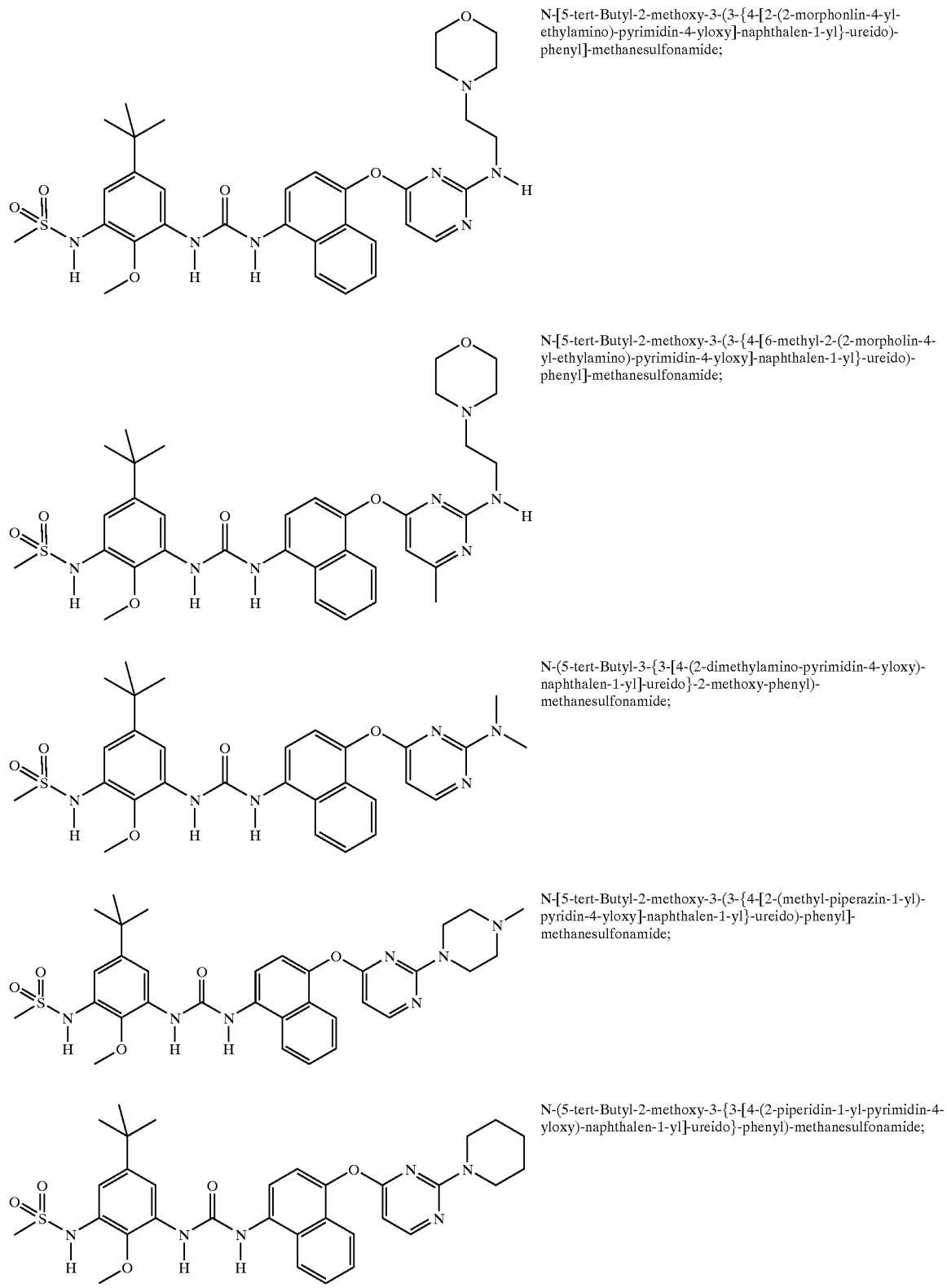

N-[5-tert-Butyl-2-methoxy-3-(3-{4-[2-(2-morpholin-4-yl-ethylamino)-pyrimidin-4-yloxy]-naphthalen-1-yl}-ureido)-phenyl]-methanesulfonamide;

N-[5-tert-Butyl-2-methoxy-3-(3-{4-[6-methyl-2-(2-morpholin-4-yl-ethylamino)-pyrimidin-4-yloxy]-naphthalen-1-yl}-ureido)-phenyl]-methanesulfonamide;

N-(5-tert-Butyl-3-{3-[4-(2-dimethylamino-pyrimidin-4-yloxy)-naphthalen-1-yl]-ureido}-2-methoxy-phenyl)-methanesulfonamide;

N-[5-tert-Butyl-2-methoxy-3-(3-{4-[2-(methyl-piperazin-1-yl)-pyridin-4-yloxy]-naphthalen-1-yl}-ureido)-phenyl]-methanesulfonamide;

N-(5-tert-Butyl-2-methoxy-3-{3-[4-(2-piperidin-1-yl-pyrimidin-4-yloxy)-naphthalen-1-yl]-ureido}-phenyl)-methanesulfonamide;

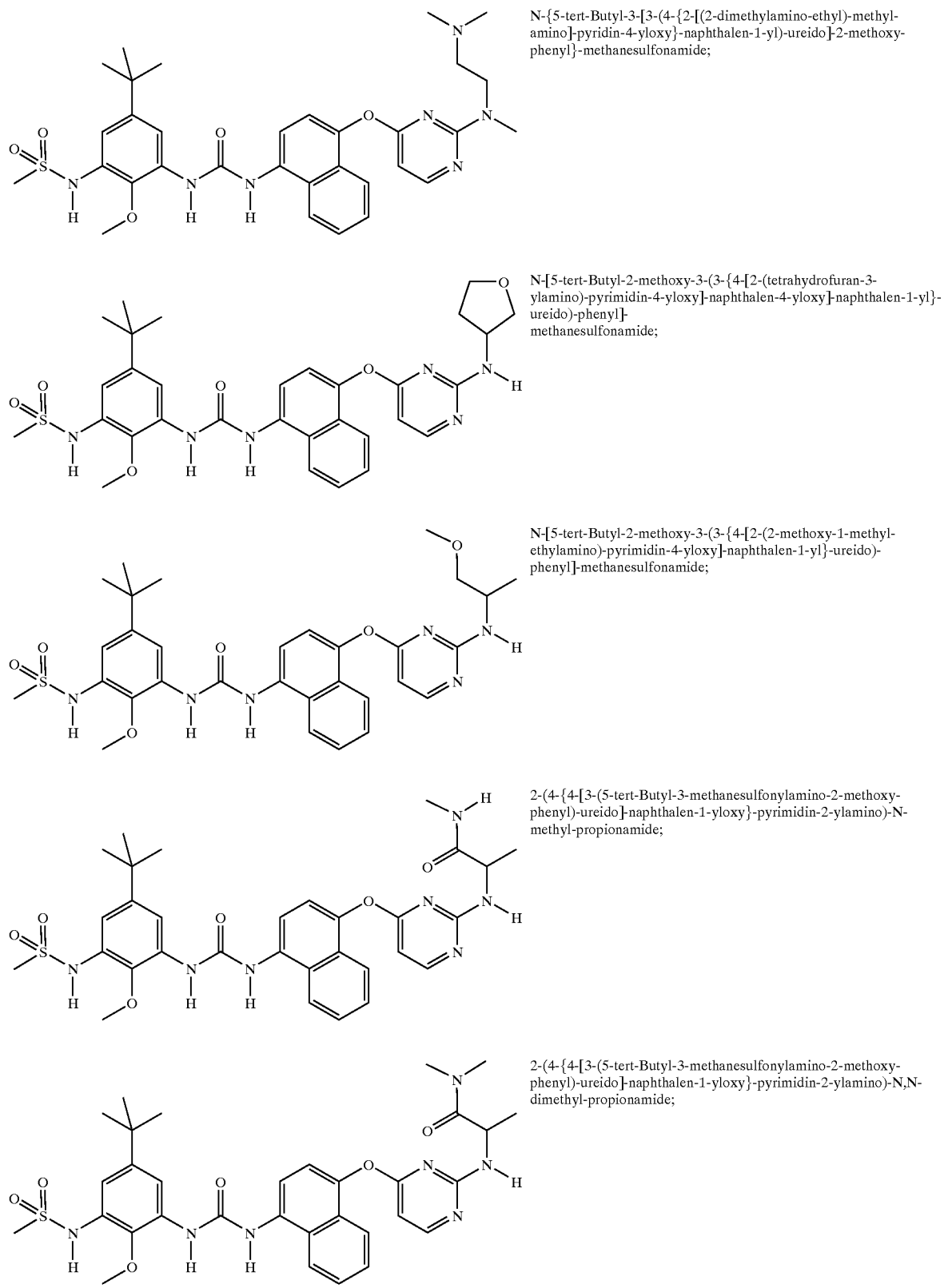

N-{5-tert-Butyl-3-[3-(4-{2-[(2-dimethylamino-ethyl)-methyl-amino]-pyridin-4-yloxy}-naphthalen-1-yl)-ureido]-2-methoxy-phenyl}-methanesulfonamide;

N-[5-tert-Butyl-2-methoxy-3-(3-{4-[2-(tetrahydrofuran-3-ylamino)-pyrimidin-4-yloxy]-naphthalen-4-yloxy]-naphthalen-1-yl}-ureido)-phenyl]-methanesulfonamide;

N-[5-tert-Butyl-2-methoxy-3-(3-{4-[2-(2-methoxy-1-methyl-ethylamino)-pyrimidin-4-yloxy]-naphthalen-1-yl}-ureido)-phenyl]-methanesulfonamide;

2-(4-{4-[3-(5-tert-Butyl-3-methanesulfonylamino-2-methoxy-phenyl)-ureido]-naphthalen-1-yloxy}-pyrimidin-2-ylamino)-N-methyl-propionamide;

2-(4-{4-[3-(5-tert-Butyl-3-methanesulfonylamino-2-methoxy-phenyl)-ureido]-naphthalen-1-yloxy}-pyrimidin-2-ylamino)-N,N-dimethyl-propionamide;

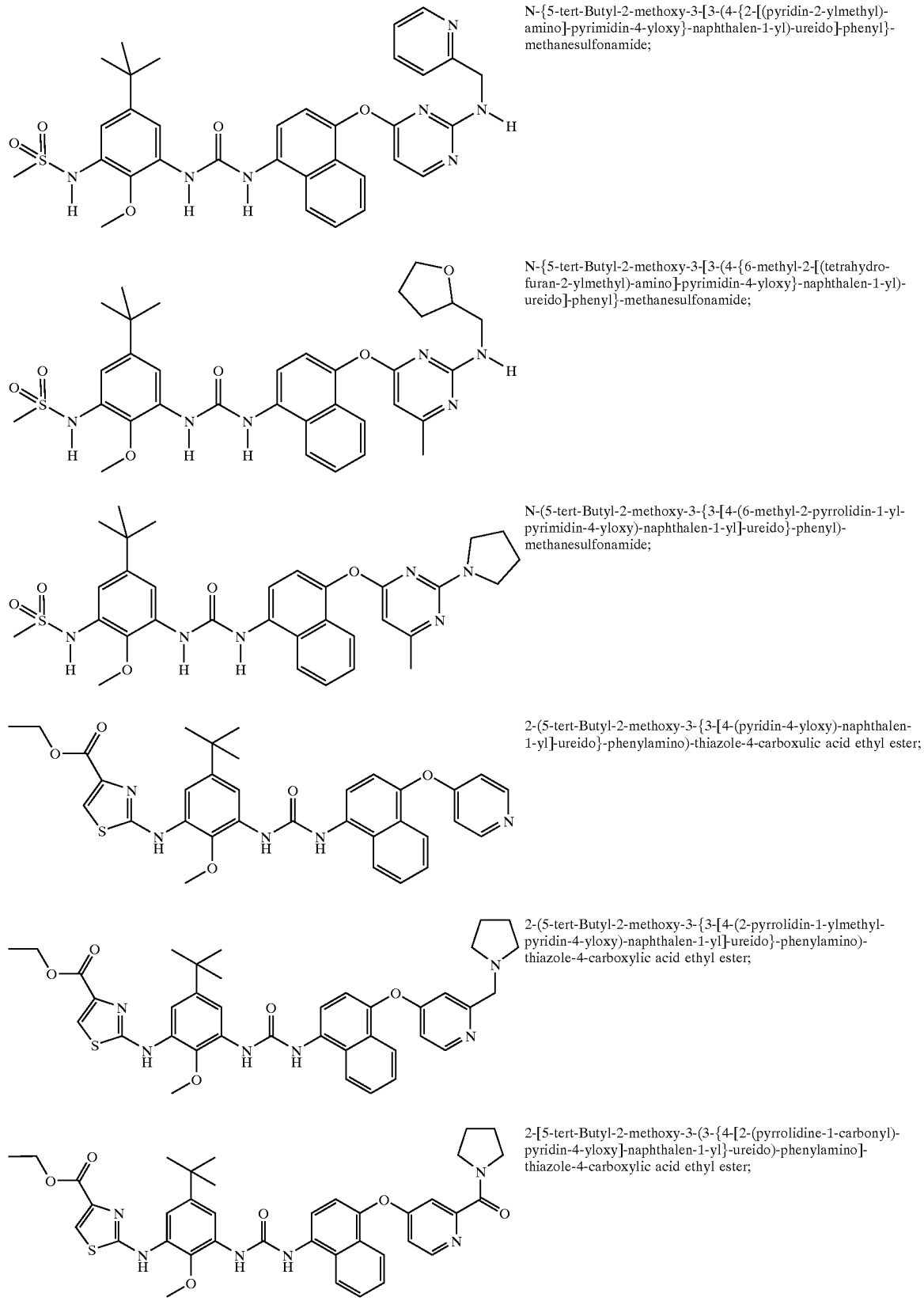

N-{5-tert-Butyl-2-methoxy-3-[3-(4-{2-[(pyridin-2-ylmethyl)-amino]-pyrimidin-4-yloxy}-naphthalen-1-yl)-ureido]-phenyl}-methanesulfonamide;

N-{5-tert-Butyl-2-methoxy-3-[3-(4-{6-methyl-2-[(tetrahydro-furan-2-ylmethyl)-amino]-pyrimidin-4-yloxy}-naphthalen-1-yl)-ureido]-phenyl}-methanesulfonamide;

N-(5-tert-Butyl-2-methoxy-3-{3-[4-(6-methyl-2-pyrrolidin-1-yl-pyrimidin-4-yloxy)-naphthalen-1-yl]-ureido}-phenyl)-methanesulfonamide;

2-(5-tert-Butyl-2-methoxy-3-{3-[4-(pyridin-4-yloxy)-naphthalen-1-yl]-ureido}-phenylamino)-thiazole-4-carboxulic acid ethyl ester;

2-(5-tert-Butyl-2-methoxy-3-{3-[4-(2-pyrrolidin-1-ylmethyl-pyridin-4-yloxy)-naphthalen-1-yl]-ureido}-phenylamino)-thiazole-4-carboxylic acid ethyl ester;

2-[5-tert-Butyl-2-methoxy-3-(3-{4-[2-(pyrrolidine-1-carbonyl)-pyridin-4-yloxy]-naphthalen-1-yl}-ureido)-phenylamino]-thiazole-4-carboxylic acid ethyl ester;

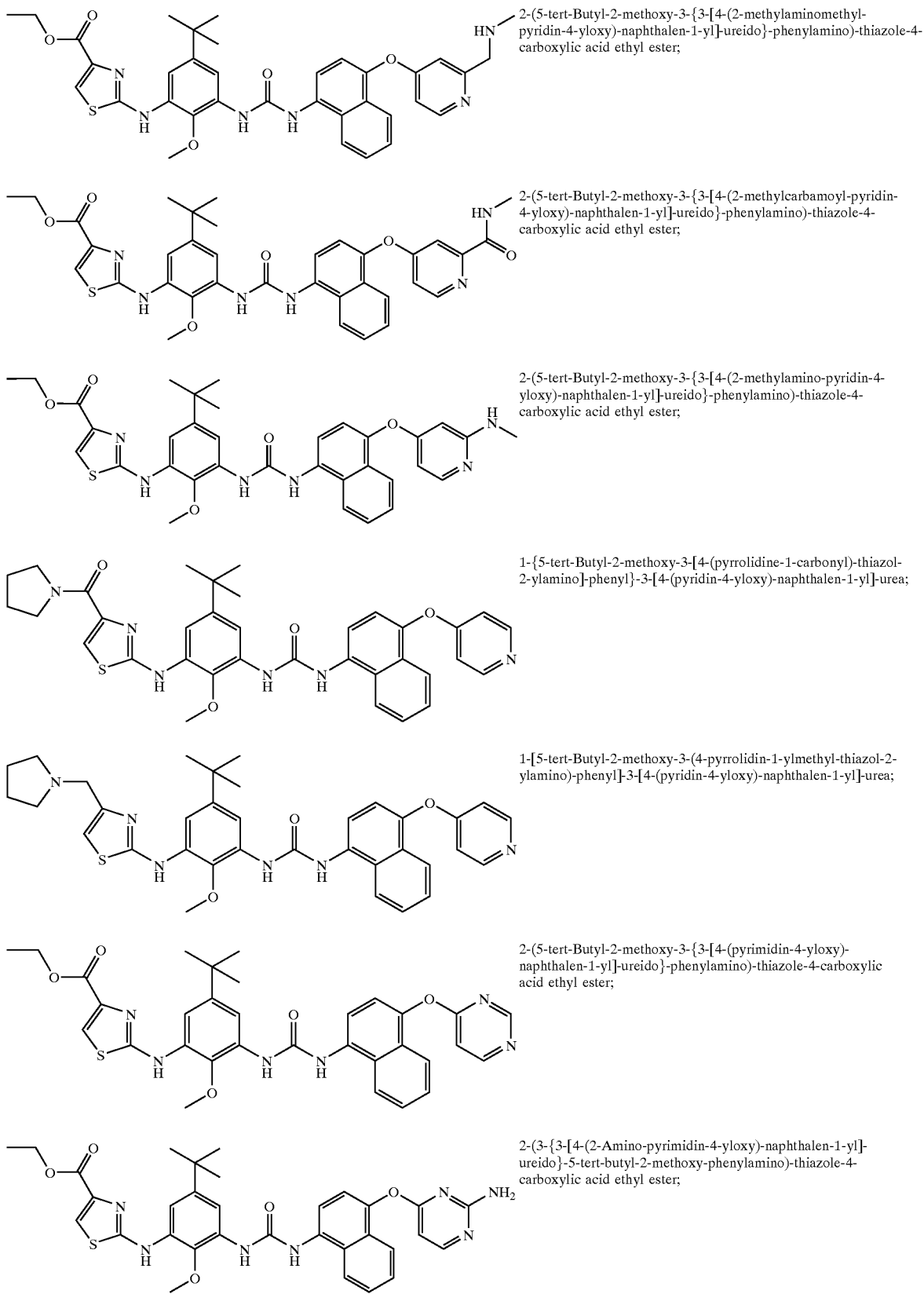

2-(5-tert-Butyl-2-methoxy-3-{3-[4-(2-methylaminomethyl-pyridin-4-yloxy)-naphthalen-1-yl]-ureido}-phenylamino)-thiazole-4-carboxylic acid ethyl ester;

2-(5-tert-Butyl-2-methoxy-3-{3-[4-(2-methylcarbamoyl-pyridin-4-yloxy)-naphthalen-1-yl]-ureido}-phenylamino)-thiazole-4-carboxylic acid ethyl ester;

2-(5-tert-Butyl-2-methoxy-3-{3-[4-(2-methylamino-pyridin-4-yloxy)-naphthalen-1-yl]-ureido}-phenylamino)-thiazole-4-carboxylic acid ethyl ester;

1-{5-tert-Butyl-2-methoxy-3-[4-(pyrrolidine-1-carbonyl)-thiazol-2-ylamino]-phenyl}-3-[4-(pyridin-4-yloxy)-naphthalen-1-yl]-urea;

1-[5-tert-Butyl-2-methoxy-3-(4-pyrrolidin-1-ylmethyl-thiazol-2-ylamino)-phenyl]-3-[4-(pyridin-4-yloxy)-naphthalen-1-yl]-urea;

2-(5-tert-Butyl-2-methoxy-3-{3-[4-(pyrimidin-4-yloxy)-naphthalen-1-yl]-ureido}-phenylamino)-thiazole-4-carboxylic acid ethyl ester;

2-(3-{3-[4-(2-Amino-pyrimidin-4-yloxy)-naphthalen-1-yl]-ureido}-5-tert-butyl-2-methoxy-phenylamino)-thiazole-4-carboxylic acid ethyl ester;

-continued

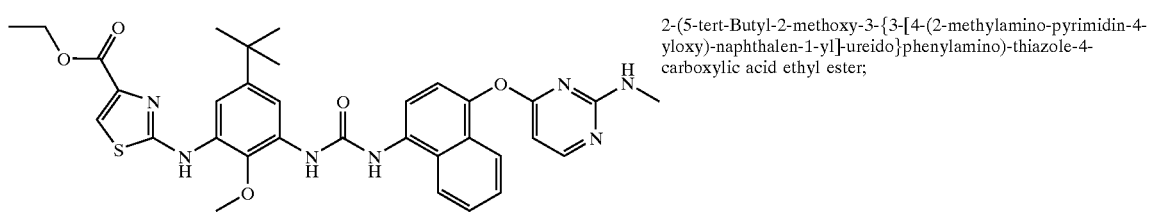
2-(5-tert-Butyl-2-methoxy-3-{3-[4-(2-methylamino-pyrimidin-4-yloxy)-naphthalen-1-yl]-ureido}phenylamino)-thiazole-4-carboxylic acid ethyl ester;

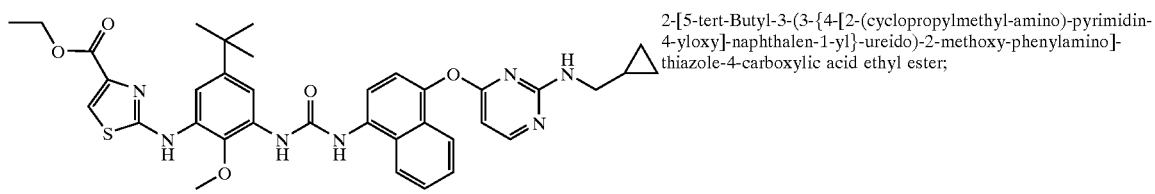
2-[5-tert-Butyl-3-(3-{4-[2-(cyclopropylmethyl-amino)-pyrimidin-4-yloxy]-naphthalen-1-yl}-ureido)-2-methoxy-phenylamino]-thiazole-4-carboxylic acid ethyl ester;

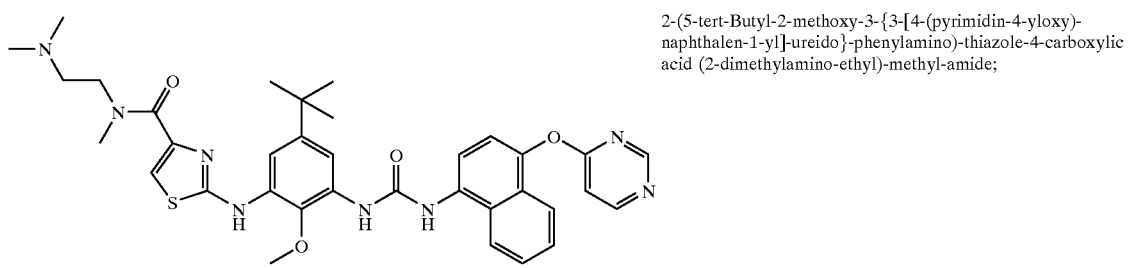
2-(5-tert-Butyl-2-methoxy-3-{3-[4-(pyrimidin-4-yloxy)-naphthalen-1-yl]-ureido}-phenylamino)-thiazole-4-carboxylic acid (2-dimethylamino-ethyl)-methyl-amide;

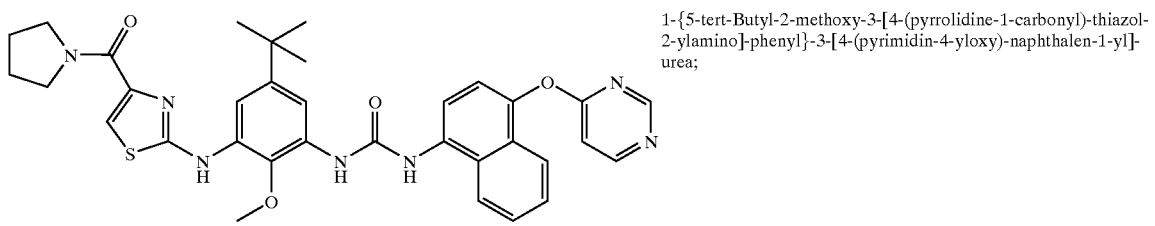
1-{5-tert-Butyl-2-methoxy-3-[4-(pyrrolidine-1-carbonyl)-thiazol-2-ylamino]-phenyl}-3-[4-(pyrimidin-4-yloxy)-naphthalen-1-yl]-urea;

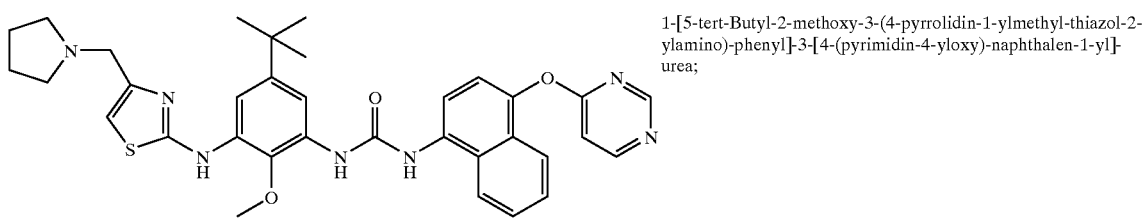
1-[5-tert-Butyl-2-methoxy-3-(4-pyrrolidin-1-ylmethyl-thiazol-2-ylamino)-phenyl]-3-[4-(pyrimidin-4-yloxy)-naphthalen-1-yl]-urea;

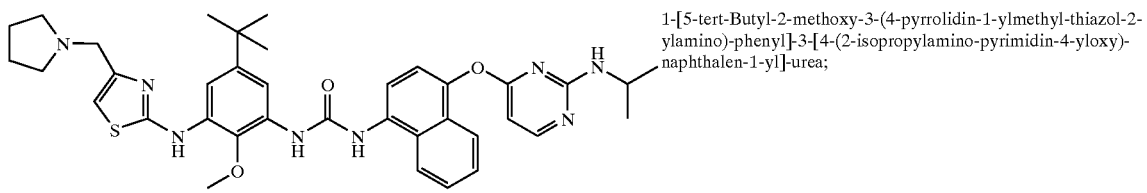
1-[5-tert-Butyl-2-methoxy-3-(4-pyrrolidin-1-ylmethyl-thiazol-2-ylamino)-phenyl]-3-[4-(2-isopropylamino-pyrimidin-4-yloxy)-naphthalen-1-yl]-urea;

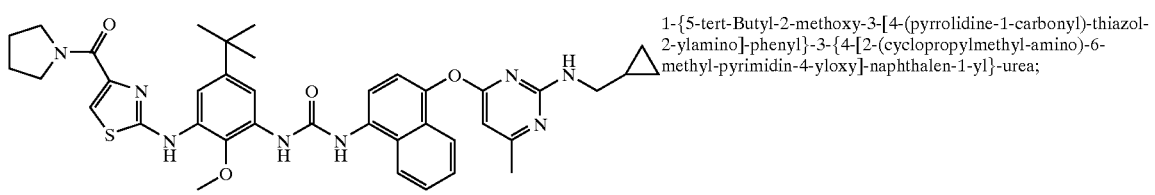
1-{5-tert-Butyl-2-methoxy-3-[4-(pyrrolidine-1-carbonyl)-thiazol-2-ylamino]-phenyl}-3-{4-[2-(cyclopropylmethyl-amino)-6-methyl-pyrimidin-4-yloxy]-naphthalen-1-yl}-urea;

-continued

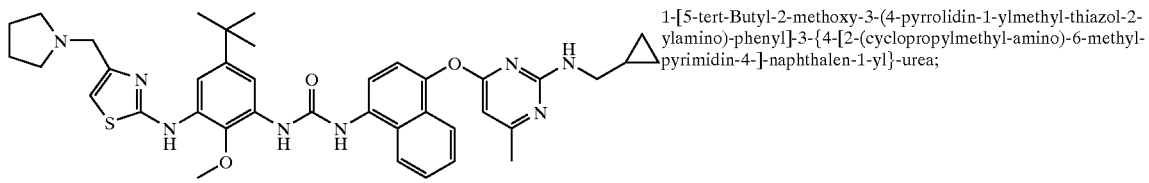
1-[5-tert-Butyl-2-methoxy-3-(4-pyrrolidin-1-ylmethyl-thiazol-2-ylamino)-phenyl]-3-{4-[2-(cyclopropylmethyl-amino)-6-methyl-pyrimidin-4-]-naphthalen-1-yl}-urea;

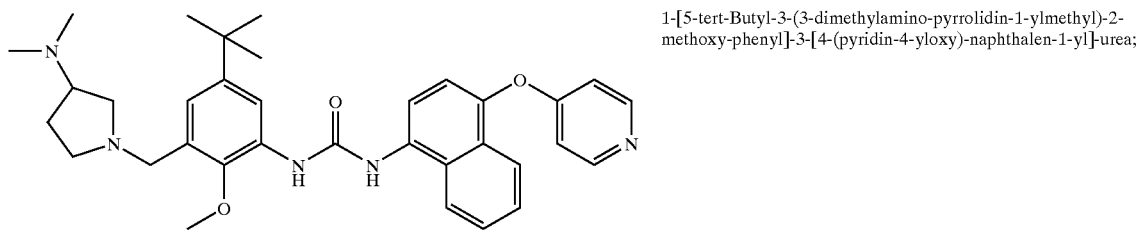
1-[5-tert-Butyl-3-(3-dimethylamino-pyrrolidin-1-ylmethyl)-2-methoxy-phenyl]-3-[4-(pyridin-4-yloxy)-naphthalen-1-yl]-urea;

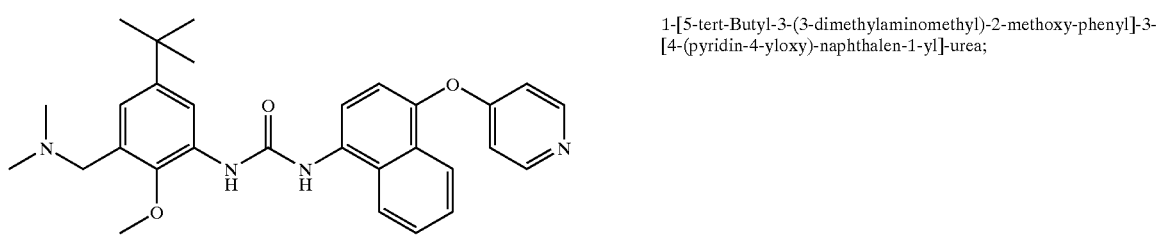
1-[5-tert-Butyl-3-(3-dimethylaminomethyl)-2-methoxy-phenyl]-3-[4-(pyridin-4-yloxy)-naphthalen-1-yl]-urea;

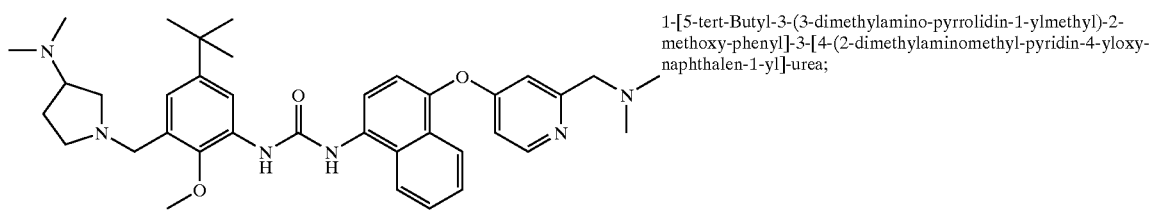
1-[5-tert-Butyl-3-(3-dimethylamino-pyrrolidin-1-ylmethyl)-2-methoxy-phenyl]-3-[4-(2-dimethylaminomethyl-pyridin-4-yloxy-naphthalen-1-yl]-urea;

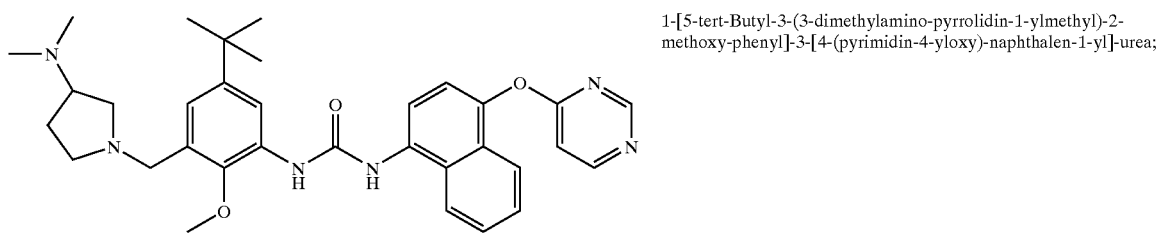
1-[5-tert-Butyl-3-(3-dimethylamino-pyrrolidin-1-ylmethyl)-2-methoxy-phenyl]-3-[4-(pyrimidin-4-yloxy)-naphthalen-1-yl]-urea;

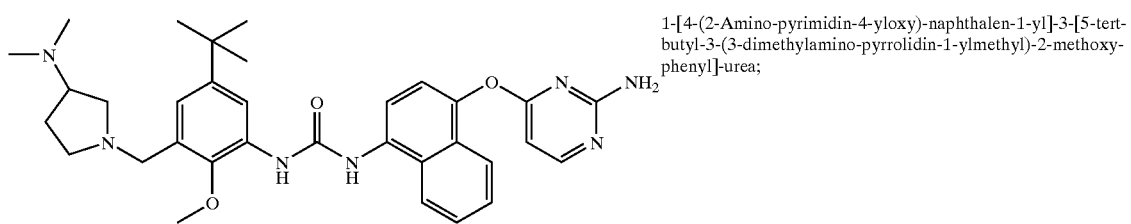
1-[4-(2-Amino-pyrimidin-4-yloxy)-naphthalen-1-yl]-3-[5-tert-butyl-3-(3-dimethylamino-pyrrolidin-1-ylmethyl)-2-methoxy-phenyl]-urea;

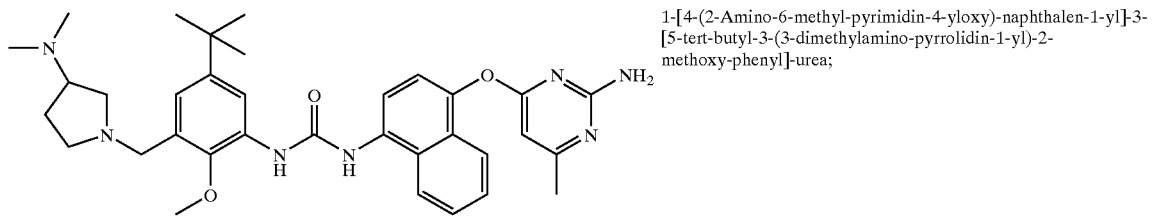
1-[4-(2-Amino-6-methyl-pyrimidin-4-yloxy)-naphthalen-1-yl]-3-[5-tert-butyl-3-(3-dimethylamino-pyrrolidin-1-yl)-2-methoxy-phenyl]-urea;

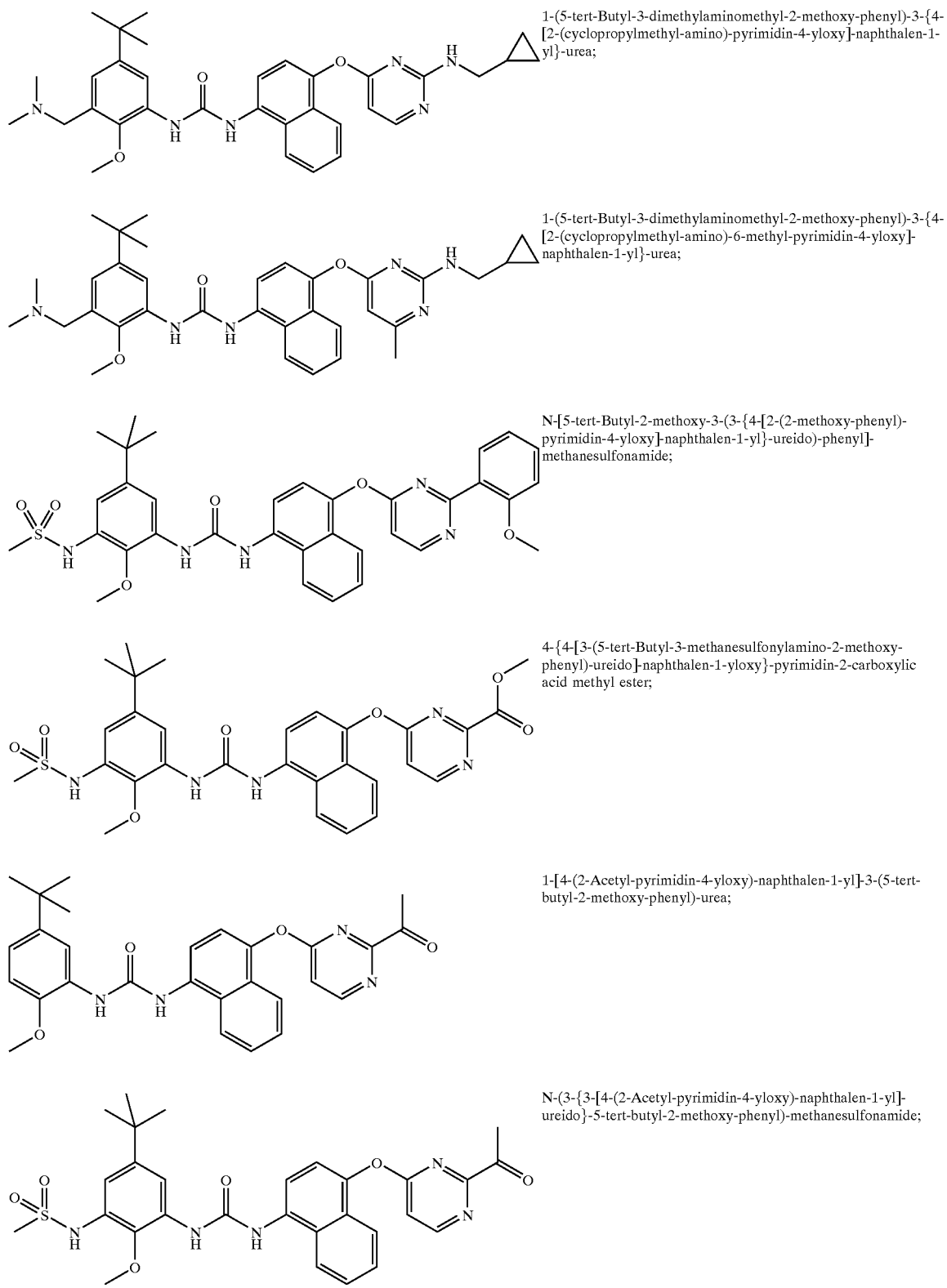

1-(5-tert-Butyl-3-dimethylaminomethyl-2-methoxy-phenyl)-3-{4-[2-(cyclopropylmethyl-amino)-pyrimidin-4-yloxy]-naphthalen-1-yl}-urea;

1-(5-tert-Butyl-3-dimethylaminomethyl-2-methoxy-phenyl)-3-{4-[2-(cyclopropylmethyl-amino)-6-methyl-pyrimidin-4-yloxy]-naphthalen-1-yl)-urea;

N-[5-tert-Butyl-2-methoxy-3-(3-{4-[2-(2-methoxy-phenyl)-pyrimidin-4-yloxy]-naphthalen-1-yl}-ureido)-phenyl]-methanesulfonamide;

4-{4-[3-(5-tert-Butyl-3-methanesulfonylamino-2-methoxy-phenyl)-ureido]-naphthalen-1-yloxy}-pyrimidin-2-carboxylic acid methyl ester;

1-[4-(2-Acetyl-pyrimidin-4-yloxy)-naphthalen-1-yl]-3-(5-tert-butyl-2-methoxy-phenyl)-urea;

N-(3-{3-[4-(2-Acetyl-pyrimidin-4-yloxy)-naphthalen-1-yl]-ureido}-5-tert-butyl-2-methoxy-phenyl)-methanesulfonamide;

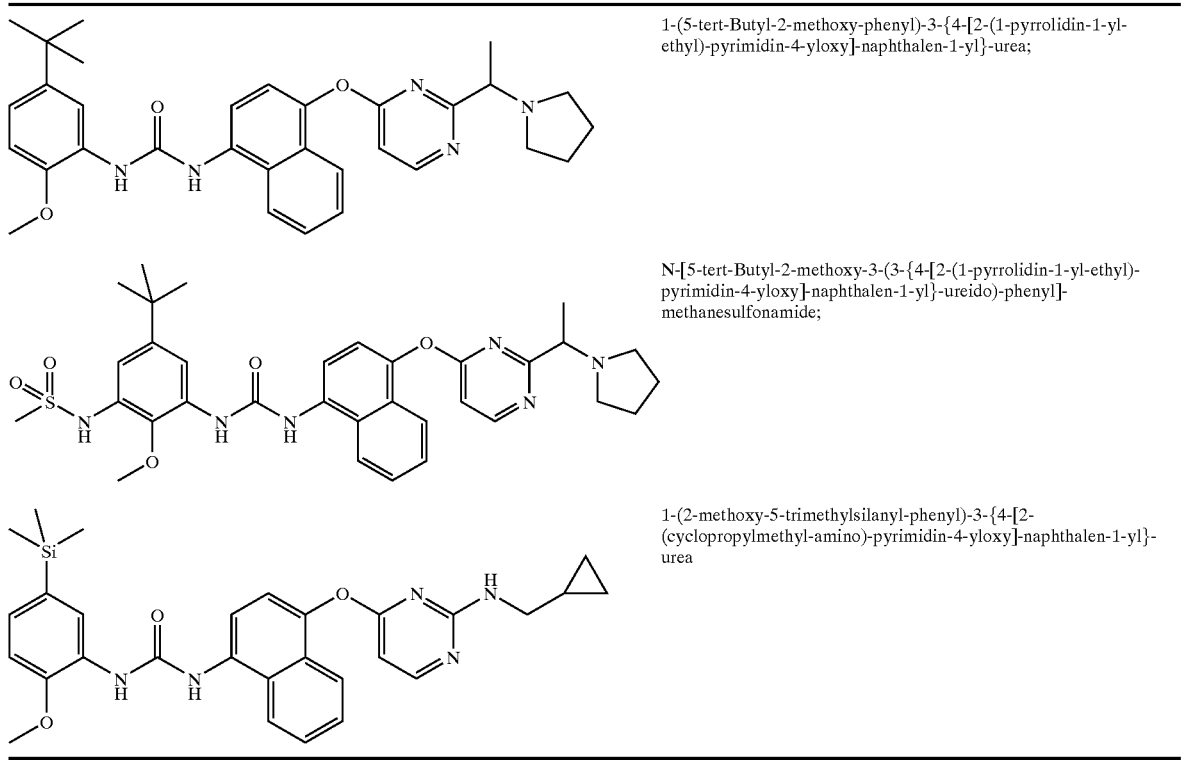

1-(5-tert-Butyl-2-methoxy-phenyl)-3-{4-[2-(1-pyrrolidin-1-yl-ethyl)-pyrimidin-4-yloxy]-naphthalen-1-yl}-urea;

N-[5-tert-Butyl-2-methoxy-3-(3-{4-[2-(1-pyrrolidin-1-yl-ethyl)-pyrimidin-4-yloxy]-naphthalen-1-yl}-ureido)-phenyl]-methanesulfonamide;

1-(2-methoxy-5-trimethylsilanyl-phenyl)-3-{4-[2-(cyclopropylmethyl-amino)-pyrimidin-4-yloxy]-naphthalen-1-yl}-urea or the pharmaceutically acceptable derivatives thereof.

In all compounds disclosed above, in the event the nomenclature in in conflict with the structure, it shall be understood that the compound is defined by the structure.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes all such tautomers. It shall also be understood that the invention includes all homologs, analogs, optical and positional isomers thereof.

All terms as used herein in this specification, unless otherwise stated, shall be understood in their ordinary meaning as known in the art.

Any of the aromatic ring systems, carbocyclic or heterocyclic, shall be understood to include the non-aromatic ring systems which may be mono- or polyunsaturated, and the positional isomers or analogs thereof.

Any of the compounds described hereinabove possessing "nitrogen" and "sulfur" shall include any oxidized form of nitrogen and sulfur and the quaternized form of any basic nitrogen.

The compounds of the invention are only those which are contemplated to be 'chemically stable' as will be appreciated by those skilled in the art. For example, a compound which would have a 'dangling valency', or a 'carbanion' are not compounds contemplated by the invention.

The invention includes pharmaceutically acceptable derivatives of the novel compounds disclosed herein. A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof. A pharmacologically active metabolite shall be understood to mean any of the novel compounds disclosed herein capable of being metabolized enzymatically or chemically. This includes, for example, hydroxylated or oxidized derivative compounds.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and $N$-$(C_1$–$C_4$ alkyl$)_4^+$ salts.

In addition, the compounds of this invention include prodrugs of compounds of the the novel compounds disclosed herein. Prodrugs include those compounds that, upon simple chemical transformation, are modified to produce compounds of the invention. Simple chemical transformations include hydrolysis, oxidation and reduction. Specifically, when a prodrug of this invention is administered to a patient, the prodrug may be transformed into a novel compound of the invention, thereby imparting the desired pharmacological effect.

METHODS OF USE

In accordance with the invention, there are provided methods of using the compounds of the invention. The compounds of the invention effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds of the invention are useful for the treatment of such conditions. These encompass diseases including, but not limited to, rheumatoid arthritis, osteoarthritis, traumatic arthritis, multiple sclerosis, Guillain-Barre syndrome, Crohn's disease, ulcerative colitis, psoriasis, graft versus host disease, systemic lupus erythematosus, glomerulonephritis, reperfusion injury, sepsis, bone resorption diseases including osteoporosis, chronic obstructive pulmonary disease, congestive heart failure, Alzheimer's disease, atherosclerosis, toxic shock syndrome, asthma, contact dermatitis, percutaneous transluminal coronary angioplasty (PTCA) and insulin-dependent diabetes mellitus.

In addition, the compounds of the invention being inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, the present novel compounds would be expected to exhibit efficacy against those disorders currently treated with COX inhibitors such as the familiar NSAIDs. These disorders include acute and chronic pain as well as symptoms of inflammation and cardiovascular disease.

As discussed in the Background of the Invention, IL-8 plays a role in the influx of neutrophils into sites of inflammation or injury. Therefore, in a yet further aspect of the invention, the compounds of the invention may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing entrerocolitis.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of the invention (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

GENERAL SYNTHETIC METHODS

The invention additionally provides for methods of making the compounds of the the invention. The compounds of the invention and intermediates used in their preparation may be prepared by the general methods and examples presented below, and methods known to those of ordinary skill in the art. Further reference in this regard may be made to the general methods and examples found in U.S. Pat. Nos. 6,319,921 and 6,358,945, U.S. application Ser. Nos. 09/714, 539, 09/611,109, 09/698,442, 09/834,797 and 09/902,085, and U.S. provisional application No. 60/283,642. Each of the aforementioned are incorporated herein by reference in their entirety. In all schemes "L" in the formulas shown below shall be defined as moieties on the left side of the urea bond, "R" shall be understood to mean all possible moieties on the right side of the urea bond. For example, the left side 'L' and the right side 'R' of the compound

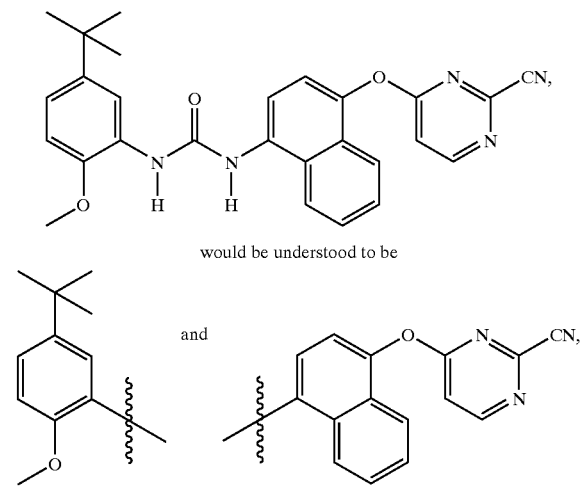

would be understood to be and respectively.

The compounds of the invention may be prepared by Method A, B, C or D as illustrated in Scheme I, preferably Method C.

Scheme I

Method A

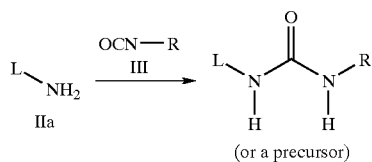

Method B

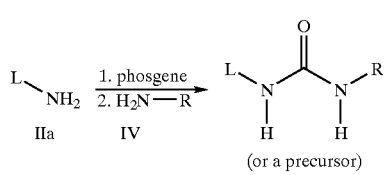

Method C

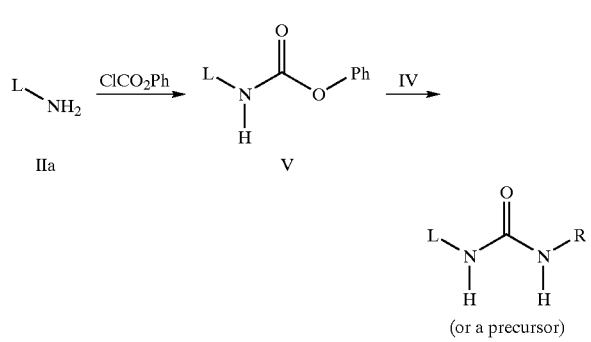

Method D

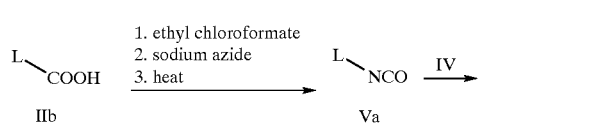

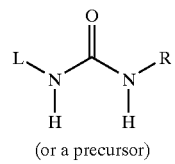

(or a precursor)

In Method A, a mixture of an arylamine of formula Ia and an arylisocyanate of formula III is dissolved in a non-protic, anhydrous solvent such as THF, ether, toluene, dioxane or ethyl acetate. The preferred solvent is THF. The mixture is stirred at between 0–45° C., preferably at 25° C., for 2–24 h, and the volatiles are removed. Purification of the residue can be accomplished by recrystallization from an appropriate solvent such as ethyl acetate/hexanes, ethyl acetate/methanol, THF/petroleum ether or ethanol/water or by silica gel chromatography, using for example, hexanes and ethyl acetate as eluents, providing the product compound or precursors thereof.

In Method B, an arylamine of formula Ia is dissolved in a halogenated solvent, such as methylene chloride, chloroform or dichloroethane. The preferred solvent is methylene chloride. The mixture is diluted with aqueous alkali, such as sodium bicarbonate or potassium carbonate, cooled in an ice bath and phosgene is added. The mixture is vigorously stirred for 5–30 min, with 10 min being preferable. The organic layer is dried, with agents such as $MgSO_4$ or $Na_2SO_4$, and the volatiles removed to provide the corresponding isocyanate. The isocyanate and arylamine IV are mixed in a non-protic, anhydrous solvent such as THF, ether, toluene, dioxane, methylene chloride or ethyl acetate. The preferred solvent is THF. The mixture is stirred at between 0–45° C., preferably at 25° C., for 2–24 h, and the volatiles are removed. Purification of the residue by recrystallization or by silica gel chromatography, as above, provides the product compound or precursors thereof.

In Method C, an arylamine of formula IIa is dissolved in a suitable halogenated solvent such as methylene chloride, chloroform or dichloroethane. The preferred solvent is methylene chloride. A suitable base such as triethylamine may be added, followed by an alkyl or aryl chloroformate, such as t-butyl chloroformate or phenyl chloroformate (shown). The mixture is stirred at between 0–85° C., preferably at reflux temperature, for 2–24 h, and the volatiles are removed providing carbamate V. The carbamate and arylamine IV are mixed in a non-protic, anhydrous solvent such as THF, ether, toluene, dioxane, methylene chloride or ethyl acetate. The preferred solvent is THF. The mixture is stirred at between 0–110° C., preferably at reflux temperature, for 2–24 h, and the volatiles are removed. Purification of the residue as above provides the product compound or precursors thereof.

In Method D, an aromatic carboxylic acid (IIb) is dissolved in a non-protic solvent, such as THF or diethyl ether, and an inorganic base, such as triethyl amine is added and the mixture is cooled to −30–0° C., with the preferred temperature being −10° C. An alkyl chloroformate, such as ethyl chloroformate, is added dropwise and the resulting mixture stirred at below room temperature, such as 0° C. for 1–3 hours. A solution of sodium azide in water is added and the mixture stirred between 1–3 hours, diluted with toluene and the organic layer dried and reduced in volume. This mixture is heated at reflux for 1–4 hours, cooled to room temperature to give isocyanate (Va) which can be reacted with amine (IV) to give the product compound or precursors thereof.

EXPERIMENTAL SECTION

Amine intermediates of formula Ia are either commercially available or may be prepared by methods known to those skilled in the art. Examples 1–4 are representative of procedures for preparing aryl amine or aryl isocyanate derivatives that may be used in Methods A–D. It will be apparent to those skilled in the art that other desired intermediates could be made by these methods by using appropriately substituted starting materials and intermediates.

EXAMPLE 1

Synthesis of 1-(5-tert-butyl-2-methoxy-phenyl)-3-[4-(2-cyano-pyrimidin-4-yloxy)-naphthalen-1-yl]-urea

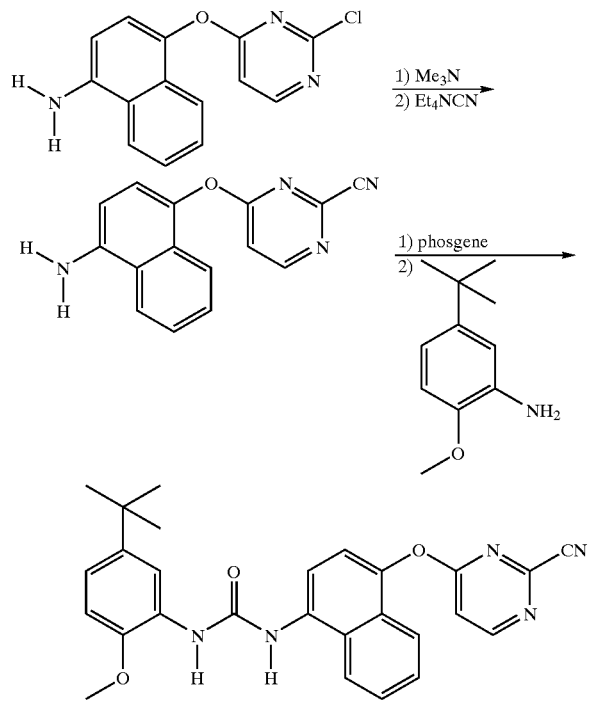

To a 0° C. solution of trimethyl amine (20% solution in water, 3.8 mmol) in 2 mL of dimethylformamide was added 4-(2-chloro-pyrimidin-4-yloxy)-naphthalen-1-ylamine (270 mg, 1 mmol). The deep tan solution was warmed to room temperature for 3 h, during which the initially light suspension became a brown suspension. After this time, tetraethylammonium cyanide (156 mg, 1 mmol) was added all at once to provide a deep amber solution. After 1 h, the reaction was quenched with water, extracted with EtOAc and dried over magnesium sulfate. Column chromatography (10–60% EtOAc-hexanes) provided 142 mg (54%) of 4-(4-amino-naphthalen-1-yloxy)-pyrimidine-2-carbonitrile.

To a 0° C. biphasic solution of the above nitrile (47 mg, 0.18 mmol) was added 0.3 mL (2.6 mmol) of phosgene. The solution was stirred for 15 min at 0° C., then warmed to room temperature for 1 h. After this time, the reaction was extracted, dried over MgSO$_4$ and concentrated in vacuo. The resulting orange solid was added to a solution of tert-butyl anisidine (75 mg, 0.35 mmol). The reaction was stirred overnight, concentrated in vacuo, and triturated with 3:1 hexanes: EtOAc to provide 55 mg (69%) of the title compound as an off-white solid.

EXAMPLE 2

Synthesis of N-(5-tert-butyl-2-methoxy-3-{3-[4-(tetrahydro-pyran-4-yloxy)-naphthalen-1-yl]-ureido}-phenyl)-methanesulfonamide

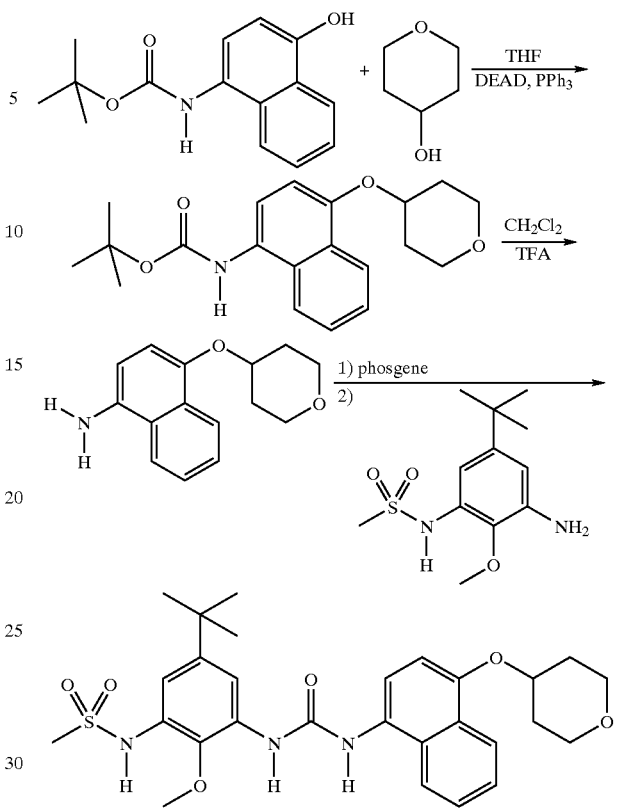

Triphenylphosphine (2.8 g, 10.8 mmol) was dissolved in THF (5 mL) and cooled to 0° C. To this colorless solution diethylazodicarboxylate (1.9 grams, 10.8 mmol) was added dropwise to afford an orange solution. After 15 min at 0° C., a copious precipitate had formed. 4-Hydroxy-naphthalen-1-yl-carbamic acid tert-butyl ester (934 mg, 3.6 mmol) and tetrahydro-4H-pyran-4-ol (552 mg, 5.4 mmol) were then added in one portion as a solution in 2 mL of THF. The purple suspension was stirred at 0° C. for one h then at room temperature for 48 h. The solvent was then evaporated and chromatographed on silica gel (40% EtOAc-hexanes) to provide 680 mg (55%) of [4-(tetrahydro-pyran-4-yloxy)-naphthalen-1-yl]-carbamic acid tert-butyl ester as a purple solid.

The above tert-butyl ester (680 mg, 1.98 mmol) was dissolved in CH$_2$Cl$_2$ (5 mL) and to the purple solution was added trifluoroacetic acid (1.14 g, 10 mmol) and the reaction was stirred overnight at room temperature. The reaction was then diluted with CH$_2$Cl$_2$ (50 mL) and washed with 50% saturated aqueous NaHCO$_3$ (50 mL). The organic portion was then washed with water, brine, dried over Na$_2$SO$_4$, and concentrated in vacuo provide 460 mg (95%) of 4-(tetrahydro-pyran-4-yloxy)-naphthalen-1-ylamine as a purple solid.

The title compound was prepared from the above amine and N-(3-amino-5-tert-butyl-2-methoxyphenyl) methanesulfonamide by the procedure described for 1-(5-tert-butyl-2-methoxy-phenyl)-3-[4-(2-cyano-pyrimidin-4-yloxy)-naphthalen-1-yl]-urea (Example 1).

EXAMPLE 3

Synthesis of 4-{4-[3-(5-tert-butyl-2-methoxy-phenyl)-ureido]-naphthalen-1-yloxy}-pyrimidine-2-carboxylic acid methyl ester

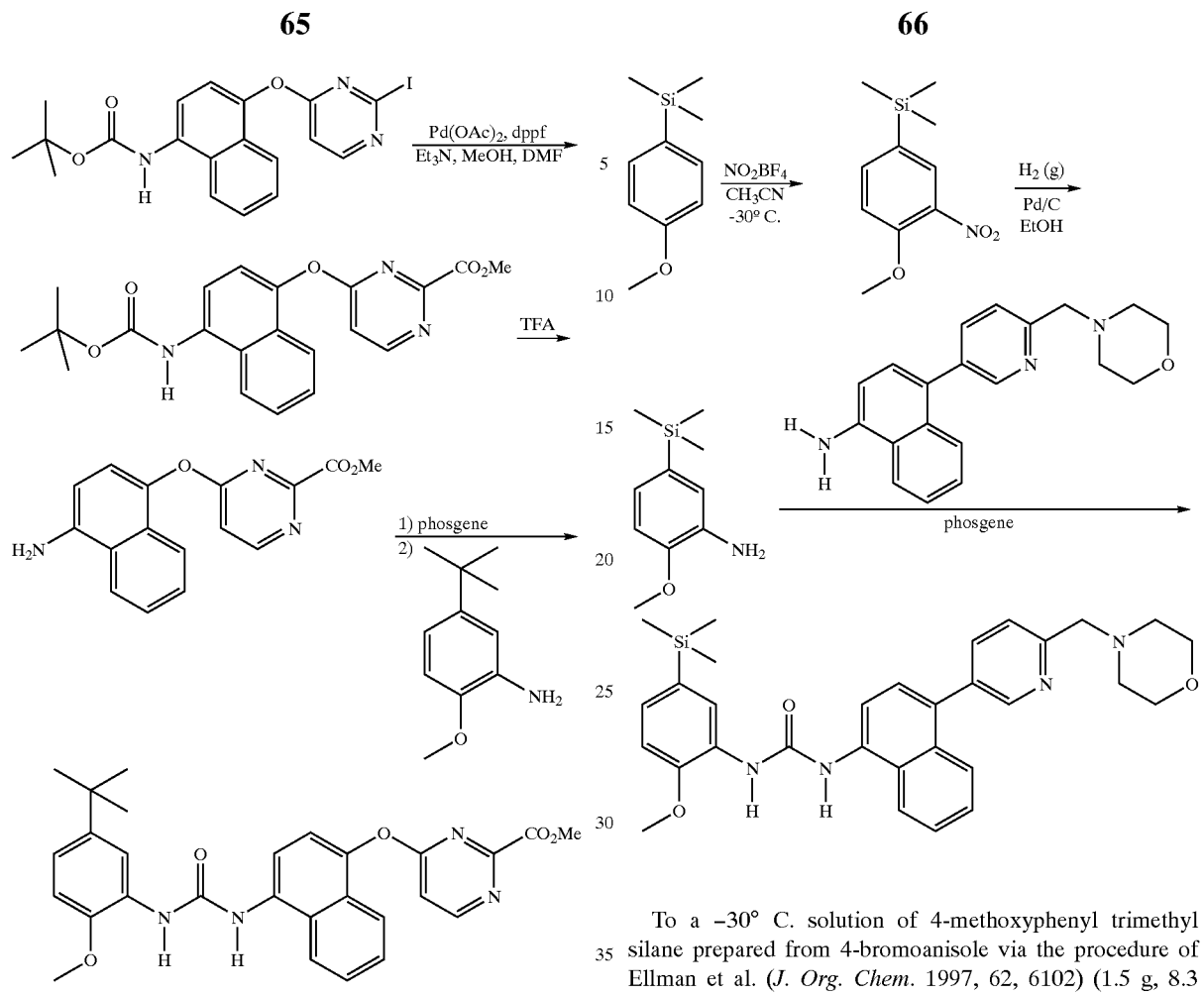

To a solution of [4-(2-iodo-pyrimidin-4-yloxy)-naphthalen-1-yl]-carbamic acid tert-butyl ester (100 mg, 0.44 mmol) in 2 mL of DMF, was added, 0.5 mL MeOH, 0.12 mL of Et$_3$N (0.9 mmol), Pd(OAc)$_2$ (10 mg, 0.04 mmol), and DPPF (44 mg, 0.4 mmol). The reaction was heated under a CO balloon at 60° C. for 5 h. The reaction was then diluted with EtOAc, concentrated in vacuo on silica gel and chromatographed directly with 10–80% EtOAc-hexanes to provide 26 mg (14%) of 4-(4-tert-butoxycarbonylamino-naphthalen-1-yloxy)-pyrimidine-2-carboxylic acid methyl ester as a brown solid.

To a solution of the above methyl ester (176 mg, 0.47 mmol) was added 5 mL of TFA. After 2 h, the reaction was concentrated in vacuo. The brown solid was suspended in toluene and concentrated in vacuo two more times. Ether trituration provided 94 mg (74%) of 4-(4-amino-naphthalen-1-yloxy)-pyrimidine-2-carboxylic acid methyl ester as a brown solid, which is used without further purification.

The title compound was prepared from the above amine and 5-tert-butyl-2-methoxyaniline by the procedure described for 1-(5-tert-butyl-2-methoxy-phenyl)-3-[4-(2-cyano-pyrimidin-4-yloxy)-naphthalen-1-yl]-urea (Example 1).

EXAMPLE 4

Synthesis of 1-(2-methoxy-5-trimethylsilanyl-phenyl)-3-[4-(6-morpholin-4-ylmethyl-pyridin-3-yl)-naphthalen-1-yl]-urea To a −30° C. solution of 4-methoxyphenyl trimethyl silane prepared from 4-bromoanisole via the procedure of Ellman et al. (*J. Org. Chem.* 1997, 62, 6102) (1.5 g, 8.3 mmol) was added NO$_2$BF$_4$ (1.1 g, 8.4 mmol) in CH$_3$CN. The resulting deep brown solution was stirred for 20 min, then water was added and the reaction was extracted with EtOAc, dried over MgSO$_4$ and concentrated in vacuo. The crude material was chromatographed on silica gel (25% EtOAc-hexanes) to provide 760 mg (40%) of (4-methoxy-3-nitro-phenyl)-trimethyl-silane as a gold oil.

The above trimethyl-silane (760 mg, 3.4 mmol) was dissolved in 25 mL of EtOH. To this was added 10% Pd/C (128 mg). The reaction was stirred for 12 h under a 1 atm balloon of hydrogen gas. The reaction was then filtered through diatomaceous earth and concentrated in vacuo to provide 400 mg (60%) of 2-methoxy-5-trimethylsilanyl-phenylamine as an amber oil which was used without further purification.

The title compound was prepared from the above amine and 4-[5-(4-aminonaphthyl)pyridin-2-ylmethyl]morpholine by the procedure described for 1-(5-tert-butyl-2-methoxy-phenyl)-3-[4-(2-cyano-pyrimidin-4-yloxy)-naphthalen-1-yl]-urea (Example 1).

EXAMPLE 5

Synthesis of 1-(5-tert-butyl-2-methoxy-phenyl)-3-[4-(2-methyl-pyrimidin-4-yloxy)-naphthalen-1-yl]-urea

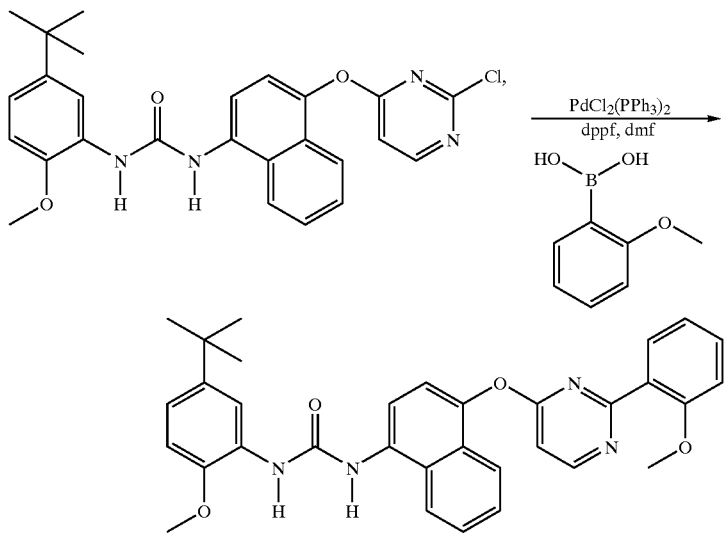

1-(5-tert-Butyl-2-methoxy-phenyl)-3-[4-(2-chloro-pyrimidin-4-yloxy)-naphthalen-1-yl]-urea (50 mg, 0.1 mmol) was dissolved in 0.4 mL of DMF. To this was added PdCl$_2$(PPh$_3$)$_2$ (10 mol %), o-methoxyboronic acid (32 mg, 0.2 mmol) in 2 mL of DME/H$_2$O/EtOH (7:3:2) and 0.53 mL of Na$_2$CO$_3$ (2M). The reaction was heated in a Smith synthesizer microwave for 3 min at 160° C. The product was concentrated on silica and purified (15–30% EtOAc-hexanes) to provide 13 mg (23%) of the title compound as an off-white foam.

EXAMPLE 6

Synthesis of 2-(5-tert-butyl-2-methoxy-3-{3-[4-(pyridin-4-yloxy)-naphthalen-1-yl]-ureido}-phenylamino)-thiazole-4-carboxylic acid ethyl ester

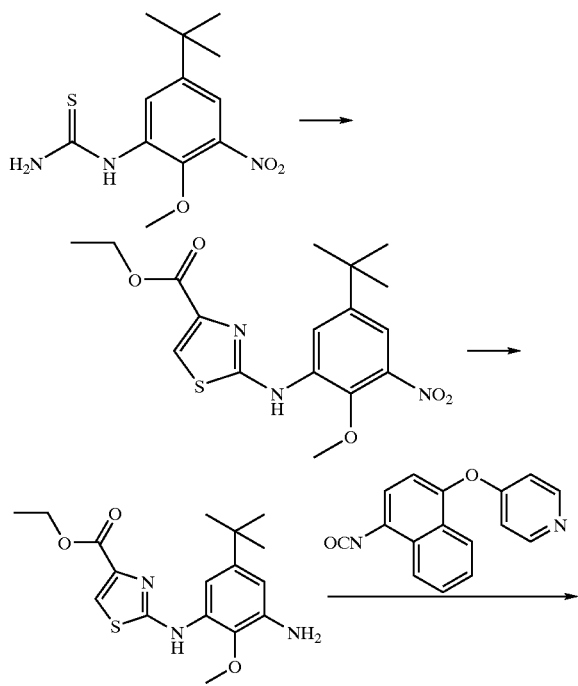

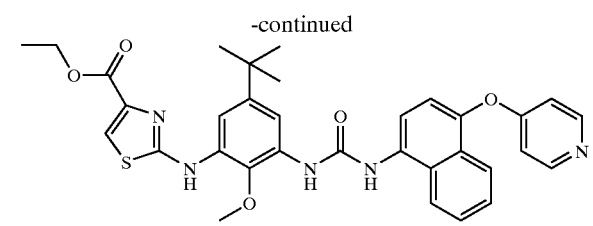

To a solution of N-(5-tert-butyl-2-methoxy-3-nitrophenyl) thiourea (1.0 g, 3.55 mmol) in EtOH (20 mL) was added bromoethylpyruvate (727 mg, 3.73 mmol). This solution was heated to reflux for 12 h. The TLC showed consumption of all starting thiourea and formation of one new product spot. The solvent was removed under vacuum and the resulting solid triturated by a mixture of hexane/EtOAc (2:1) to get the desired thiazole product as a yellow solid (1.2 g, 86% yield).

To a solution of the above thiazole (1 g, 2.66 mmol) in a mixture of THF/EtOAc (1:1, 60 mL) palladium on carbon (10%, 200 mg) was added in one portion. The black yellow suspension was subjected to hydrogen pressure (50 psi) for 16 h. The catalyst was removed by filtration through diatomaceous earth, and the resulting solution was concentrated to give the desired aniline intermediate as a thick, brown oil.

To a solution of the above aniline (100 mg, 0.29 mmol) in dichloromethane (2 mL) was added a preformed solution of 4-(pyridin-4-yloxy)-naphthalen-1-yl isocynate (250 mg, 0.86 mmol) in dichloromethane 2 mL. This solution was stirred at room temperature for 12 h. The solvent was removed by rotary evaporation and the resulting oil purified on a flash silica gel column eluting with a dichloromethane-MeOH mixture (95:5) to provide the title compound as light brown foam (50 mg, 29% yield).

EXAMPLE 7

Synthesis of 1-(5-tert-butyl-2-methoxy-phenyl)-3-[4-(2-isopropyl-6-methyl-pyrimidin-4-yloxy)-naphthalen-1-yl]-urea

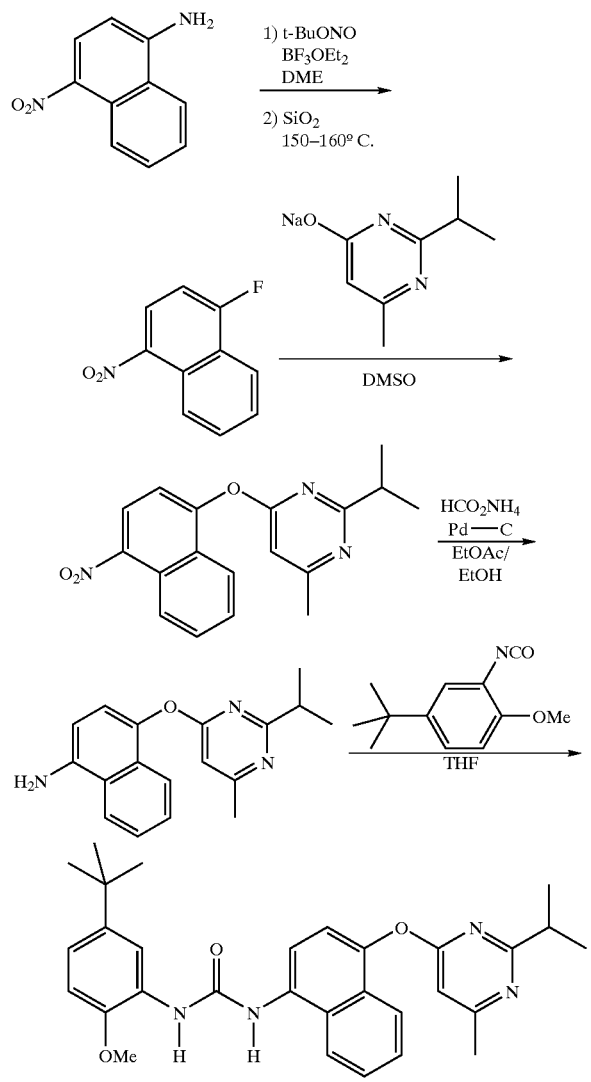

2-Isopropyl-6-methyl-4-pyrimidinol (264 mg, 1.74 mmol, 1.1 equiv.) was dissolved in 2.5 mL anhydrous DMSO. Sodium tert-butoxide (159 mg, 1.66 mmol, 1.05 equiv.) was added in one portion and the mixture was left stirring for 15 min at room temperature. Solid 4-fluoro-1-nitro-naphthalene was then added in one portion and the mixture was gently heated to 60° C. while stirring for 4 h. A color change from orange to green was noted. Saturated aqueous sodium bicarbonate solution was then added and the product extracted 3 times with EtOAc. The combined organic extracts were washed once with water and with brine, dried ($Na_2SO_4$) and filtered. The volatiles were removed in vacuo to afford a waxy orange solid. Crude yield was 459 mg (1.42 mmol or 90%). The material was used without purification for the next step.

The crude nitronaphthyl-pyrimidinyl ether from above (459 mg, 1.42 mmol, 1 equiv.) was taken up in 35 mL EtOAc and 35 mL EtOH. Ammonium formate was added (537 mg, 8.52 mmol, 6 equiv.) as well as 400 mg of 10% palladium-on-carbon. The reaction mixture was heated to a gentle reflux for one h, cooled back to room temperature, filtered through diatomaceous earth and the volatiles were removed in vacuo. The crude product was purified by chromatography on $SiO_2$, eluting with 20–40% EtOAc in hexanes. The desired aminonaphthyl-pyrimidinyl ether was isolated as a yellow foam (176 mg, 0.6 mmol, 42% for 2 steps).

5-tert-Butyl-ortho-anisidine (107 mg, 0.60 mmol, 1 equiv.) was dissolved in 25 mL dichloromethane and 20 mL saturated aqueous sodium bicarbonate solution was added. The mixture was cooled to 0° C. Without stirring, phosgene (2.0 M in toluene, 1.05 mL, 2.1 mmol, 3.5 equiv.) was added in one portion to the organic layer via syringe. After 15 min the layers were separated and the aqueous phase was extracted with one portion of dichloromethane. The combined organics were dried ($Na_2SO_4$), filtered and the majority of the solvent was removed in vacuo. To this isocyanate residue was immediately added a solution of the naphthylamino-pyrimidinyl ether from above (88 mg, 0.3 mmol, 0.5 equiv.) in 2.5 mL anhydrous THF. The mixture was left stirring at room temperature overnight, then MeOH was added and the solvents removed in vacuo. A purple foam was obtained, which was purified by column chromatography on $SiO_2$, eluting with 0–10% MeOH in dichloromethane. Recrystallization from acetonitrile/water afforded 76 mg of the title compound as a white solid (0.15 mmol, 50% yield).

Boron trifluoride etherate (4.0 mL, 31.1 mmol, 1.5 equiv.) was cooled on an ice bath under inert atmosphere in a dry round bottom flask. 4-Amino-1-nitronaphthalene (3.9 g, 20.7 mmol, 1equiv.) dissolved in 100 mL anhydrous DME was added slowly, over 10 min. After stirring 15 min, tert-butyl nitrite (3.0 mL, 24.8 mmol, 1.2 equiv.) was added dropwise via syringe. The ice bath was removed and the mixture was stirred at room temperature for 1.5 h. A precipitate of golden green color had formed. The mixture was then re-cooled to 0° C. and the precipitated 4-nitro-naphthalene diazonium tetrafluoroborate salt 5.1 g (17.7 mmol or 86%) was collected via vacuum filtration through a Buchner funnel.

The diazonium salt from above (408 mg, 1.42 mmol, 1 equiv.) was mixed with silica gel (63–200 micron, 2500 mg) and rendered homogeneous by light mixing in a mortar. This mixture was placed in a round bottom flask equipped with a mechanical stirrer and a condenser, and heated to 150–170° C. for 0.5 h. The mixture turned dark. The solid mixture was allowed to cool back to room temperature, placed on top of a short plug of silica gel, the transfer being aided by some hexanes solvent. The pure 4-fluoro-1-nitronaphthalene product was eluted with 10% EtOAc in hexanes. After removal of the solvents in vacuo 190 mg of product (0.99 mmol, 70% yield) was collected as a yellow-orange solid.

EXAMPLE 8

Synthesis of N-(3-{3-[4-(2-isopropyl-6-methyl-pyrimidin-4-yloxy)-naphthalen-1-yl]-ureido}-5-tert-butyl-2-methoxyphenyl)-methanesulfonamide

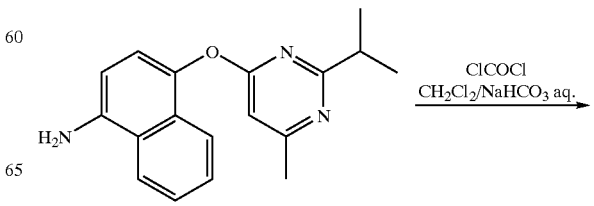

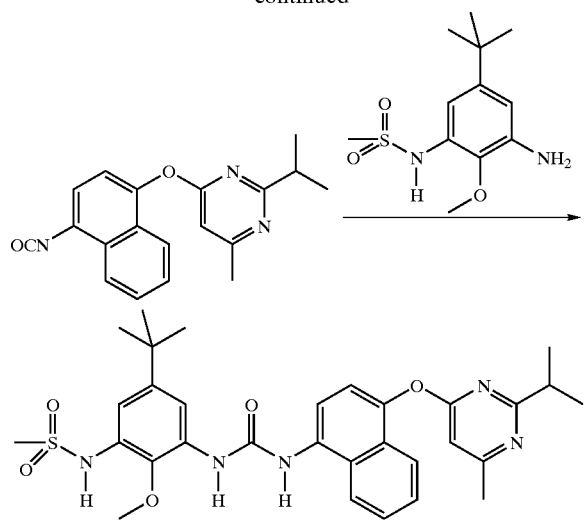

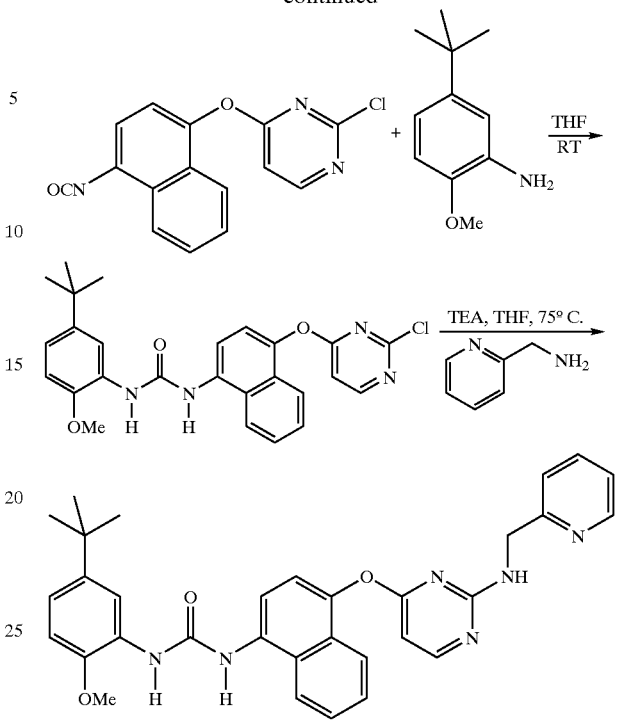

The intermediate naphthylamino-pyrimidinyl ether from Example 7 (104 mg, 0.36 mmol, 1 equiv.) was dissolved in 20 mL dichloromethane and 20 mL saturated aqueous sodium bicarbonate solution was added. The mixture was cooled to 0° C. Without stirring, phosgene (2.0 M in toluene, 0.62 mL, 1.24 mmol, 3.5 equiv.) was added in one portion to the organic layer via syringe. After 15 min the layers were separated and the aqueous phase was extracted with one portion of dichloromethane. The combined organics were dried ($Na_2SO_4$), filtered and the majority of the solvent was removed in vacuo. To this isocyanate residue was immediately added a solution of N-(3-amino-5-tert-butyl-2-methoxy-phenyl)-methanesulfonamide (97 mg, 0.36 mmol, 1 equiv.) in 2.5 mL anhydrous THF. The mixture was left stirring at room temperature overnight, then MeOH was added and the solvents removed in vacuo. A purple foam was obtained, which was purified by column chromatography on $SiO_2$, eluting with 0–10% MeOH in dichloromethane. Finally recrystallization from acetonitrile/water afforded 45 mg of the title compound as a white solid (0.08 mmol, 21% yield).

EXAMPLE 9

Synthesis of 1-(5-tert-butyl-2-methoxy-phenyl)-3-(4-{2-[(pyridin-2-ylmethyl)-amino]-pyrimidin-4-yloxy}-naphthalen-1-yl)-urea

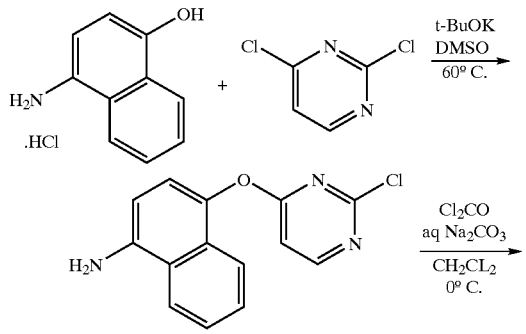

4-Aminonaphthol hydrochloride (4.40 g, 22.5 mmol, 1 equiv.) was dissolved in 30 mL anhydrous DMSO at room temperature and was treated with potassium tert-butoxide (5.05 g, 45.0 mmol, 2 equiv.). After 30 min 2,4-dichloropyrimidine (3.34 g, 22.5 mmol, 1 equiv.) in 12 mL anh. DMSO was added via cannula. Once the addition was complete, the mixture was heated to 60° C. for 3 h, then allowed to cool. Water (200 mL) was added and the product extracted with EtOAc (3×50 mL). Combined extracts were washed twice with water and once with brine, then dried ($Na_2SO_4$). A golden brown foam (6.60 g) was obtained after filtration and removal of solvents in vacuo. The crude product was purified by column chromatography on $SiO_2$ using 35% EtOAc in hexanes as eluent. The purified product was isolated as an orange solid (4.68 g, 17.2 mmol, 76% yield).

The dichloropyrimidine-naphthylamine ether from above (1.04 g, 3.83 mmol, 1 equiv.) was dissolved in 100 mL dichloromethane and 75 mL of a saturated aqueous solution of sodium bicarbonate was added. The mixture was cooled to 0° C. Without stirring, phosgene (~2 M in toluene, 6.7 mL, 13.4 mmol, 3.5 equiv.) was added via syringe to the organic layer in one portion. Stirring was resumed for 20 min, then the layers were separated. The organic layer was dried ($Na_2SO_4$), filtered, and the solvent was removed in vacuo, leaving ~5 mL of toluene. To this residue was immediately added tert-butyl-ortho-anisidine (687 mg, 3.83 mmol, 1 equiv.) in 18 mL anh. THF at room temperature, and the mixture was left stirring for 4 h. The solvents were then removed in vacuo leaving a yellow solid, which was triturated to a white powder in hot EtOAc. The intermediate chloropyrimidine-urea was thus isolated (1.23 g, 2.58 mmol, 67% yield).

The final substitutions of the chloropyrimidine from above, to afford a number of different aminopyrimidines, were carried out in parallel, and are exemplified here with 2-aminomethylpyridine.

The chloropyrimidine-urea (70 mg, 0.147 mmol, 1 equiv.) was dissolved in 1 mL anhydrous THF. Triethylamine (21

µL, 0.147 mmol, 1 equiv.) was added, followed by a 1 M solution of 2-aminomethylpyridine in THF (0.15 mL, 0.15 mmol, 1 equiv.). The mixture was sealed in a pressure tube and heated to 75° C. for 96 h. Water was added and the product extracted with EtOAc and purified by column chromatography on $SiO_2$ using 3% MeOH in dichloromethane. An orange foam was obtained and the product was further purified by recrystallization from hot $CH_3CN$ to provide the title compound (29 mg), mp 148–150° C.

ASSESSMENT OF BIOLOGICAL PROPERTIES

Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation*, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was nonsterile. Initial stock solutions were made in DMSO followed by dilution into RPMI 1640 2-fold higher than the desired final assay concentration. Confluent THP.1 cells ($2 \times 10^6$ cells/mL, final conc.; American Type Culture Company, Rockville, Md.) were added to 96 well polypropylene round bottomed culture plates (Costar 3790; sterile) containing 125 µL test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 µg/mL final; Siga L-2630, from *E. coli* serotype 011 1.B4; stored as 1 mg/mL stock in endotoxin screened distilled $H_2O$ at −80° C.). Blanks (unstimulated) received $H_2O$ vehicle; final incubation volume was 250 µl. Overnight incubation (18–24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated $IC_{50}$ value is the concentration of the test compound that caused a 50% decrease in the maximal TNFα production. Preferred compounds from those found in Table I and in the examples will exhibit an $IC_{50}$<10 M.

Inhibition of other Cytokines

By similar methods using peripheral blood monocytic cells, appropriate stimuli, and commercially available ELISA kits (or other method of detection such as radioimmunoassay), for a particular cytokine, inhibition of IL-1, G M-CSF, IL-6 and IL-8 can be demonstrated (for example, see J. C. Lee et al., 1988, *Int. J. Immunopharmacol.*, 10, 835).

What is claimed is:

1. A compound selected from the group consisting of:
  1-(5-tert-Butyl-2-methoxy-phenyl)-3-[4-(2-isopropyl-6-methyl-pyrimidin-4-yloxy)-naphthalen-1-yl]-urea;
  1-(5-tert-Butyl-2-methoxy-phenyl)-3-[4-(2,6-dimethyl-pyrimidin-4-yloxy)-naphthalen-1-yl]-urea;
  1-(5-tert-Butyl-2-methoxy-phenyl)-3-[4-(pyrimidin-4-yloxy)-naphthalen-1-yl]-urea;
  1-(5-tert-Butyl-2-methoxy-3-[1,2,4]triazol-4-yl-phenyl)-3-[4-(pyrimidin-4-yloxy)-naphthalan-1-yl]-urea;
  1-(5-tert-Butyl-2-methoxy-phenyl)-3-[4-(2-oxo-2H-pyran-4-yloxy)-naphthalen-1-yl]-urea;
  5-tert-Butyl-2-methoxy-3-{3-[4-(6-morpholin-4-ylmethyl-pyridin-3-yl)-naphthalen-1-yl]-ureido}-benzoic acid;
  Carbonic acid 5-tert-butyl-2-methoxy-3-{3-[4-(6-morpholin-4-ylmethyl-pyridin-3-yl)-naphthalen-1-yl]-ureido}-phenyl ester methyl ester;
  1-(5-tert-Butyl-2-methoxy-phenyl)-3-[4-(4-isopropylamino-[1,3,5]triazin-2-yloxy)-naphthalen-1-yl]-urea;
  1-(5-tert-Butyl-2-methoxy-phenyl)-3-{4-[4-(cyclopropylmethyl-amino)-[1,3,5]triazin-2-yloxy]-naphthalen-1-yl}-urea;
  1-[4-(4-Amino-[1,3,5]triazin-2-yloxy)-naphthalen-1-yl]-3-(5-tert-butyl-2-methoxy-phenyl)-urea;
  1-(5-tert-Butyl-2-methoxy-phenyl)-3-[4-([1,3,5]triazin-2-yloxy)-naphthalen-1-yl]-urea;
  1-(5-tert-Butyl-2-methoxy-phenyl)-3-[4-(2-cyclopropylamino-6-methyl-pyrimidin-4-yloxy)-naphthalen-1-yl]-urea;
  1-(5-tert-Butyl-2-methoxy-phenyl)-3-[4-(2-methylamino-pyrimidin-4-yloxy)-naphthalen-1-yl]-urea;
  1-(5-tert-Butyl-2-methoxy-phenyl)-3-[4-(2-ethylamino-pyrimidin-4-yloxy)-naphthalen-1-yl]-urea;
  1-(5-tert-Butyl-2-methoxy-phenyl)-3-[4-(6-methyl-2-methylamino-pyrimidin-4-yloxy)-naphthalen-1-yl]-urea;
  1-[4-(2-Amino-6-methyl-pyrimidin-4-yloxy)-naphthalen-1-yl]-3-(5-tert-butyl-2-methoxy-phenyl)-urea;
  1-[4-(2-Amino-pyrimidin-4-yloxy)-naphthalen-1-yl]-3-(5-tert-butyl-2-methoxy-phenyl)-urea;
  1-(5-tert-Butyl-2-methoxy-phenyl)-3-[4-(2-cyclopentylamino-pyrimidin-4-yloxy)-naphthalen-1-yl]-urea;
  1-(5-tert-Butyl-2-methoxy-phenyl)-3-{4-[2-(cyclopropylmethyl-amino)-pyrimidin-4-yloxy]-naphthalen-1-yl}-urea;
  1-(5-tert-Butyl-2-methoxy-phenyl)-3-{4-[2-(cyclopropylmethyl-amino)-6-methyl-pyrimidin-4-yloxy]-naphthalen-1-yl}-urea;
  1-(5-tert-Butyl-2-methoxy-phenyl)-3-(4-{2-[(tetrahydrofuran-2-ylmethyl)-amino]-pyrimidin-4-yloxy}-naphthalen-1-yl)-urea;
  1-(5-tert-Butyl-2-methoxy-phenyl)-3-(4-{2-[(pyridin-2-ylmethyl)-amino]-pyrimidin-4-yloxy}-naphthalen-1-yl)-urea;
  1-(5-tert-Butyl-2-methoxy-phenyl)-3-{4-[2-(2-morpholin-4-yl-ethylamino)-pyrimidin-4-yloxy]-naphthalen-1-yl}-urea;
  1-[4-(2-Benzylamino-pyrimidin-4-yloxy)-naphthalen-1-yl]-3-(5-tert-butyl-2-methoxy-phenyl)-urea;
  1-[4-(2-sec-Butylamino-pyrimidin-4-yloxy)-naphthalen-1-yl]-3-(5-tert-butyl-2-methoxy-phenyl)-urea;
  1-(5-tert-Butyl-2-methoxy-phenyl)-3-{4-[2-(2-methoxy-ethylamino)-pyrimidin-4-yloxy]-naphthalen-1-yl}-urea;
  1-(5-tert-Butyl-2-methoxy-phenyl)-3-{4-[2-(2-dimethylamino-ethylamino)-pyrimidin-4-yloxy]-naphthalen-1-yl}-urea;
  1-(5-tert-Butyl-2-methoxy-phenyl)-3-[4-(2-dimethylamino-pyrimidin-4-yloxy)-naphthalen-1-yl]-urea;
  1-(5-tert-Butyl-2-methoxy-phenyl)-3-[4-(2-pyrrolidin-1-yl-pyrimidin-4-yloxy)-naphthalen-1-yl]-urea;

1-(5-tert-Butyl-2-methoxy-phenyl)-3-[4-(6-methyl-2-pyrrolidin-1-yl-pyrimidin-4-yloxy)-naphthalen-1-yl]-urea;

1-(5-tert-Butyl-2-methoxy-phenyl)-3-[4-(2-morpholin-4-yl-pyrimidin-4-yloxy)-naphthalen-1-yl]-urea;

1-(5-tert-Butyl-2-methoxy-phenyl)-3-{4-[2-(4-methyl-piperazin-1-yl)-pyrimidin-4-yloxy]-naphthalen-1-yl}-urea;

1-(5-tert-Butyl-2-methoxy-phenyl)-3-[4-(2-ethoxy-pyrimidin-4-yloxy)-naphthalen-1-yl]-urea;

1-(5-tert-Butyl-2-methoxy-phenyl)-3-{4-[2-(2-morpholin-4-yl-ethoxy)-pyrimidin-4-yloxy]-naphthalen-1-yl}-urea;

1-(5-tert-Butyl-2-methoxy-phenyl)-3-{4-[2-(2-dimethylamino-ethoxy)-pyrimidin-4-yloxy]-naphthalen-1-yl}-urea;

1-[4-(2-Benzylamino-pyrimidin-4-yloxy)-naphthalen-1-yl]-3-(5-tert-butyl-2-methoxy-3-[1,2,4]triazol-4-yl-phenyl)-urea;

1-(5-tert-Butyl-2-methoxy-phenyl)-3-[4-(2-methanesulfinyl-pyrimidin-4-yloxy)-naphthalen-1-yl]-urea;

1-(5-tert-Butyl-2-methoxy-phenyl)-3-[4-(2-methylsulfanyl-pyrimidin-4-yloxy)-naphthalen-1-yl]-urea;

1-(2-Methoxy-5-trimethylsilanyl-phenyl)-3-[4-(6-morpholin-4-ylmethyl-pyridin-3-yl)-naphthalen-1-yl]-urea;

1-(5-tert-Butyl-2-methoxy-phenyl)-3-{4-[2-(2-methoxy-phenyl)-pyrimidin-4-yloxy]-naphthalen-1-yl}-urea;

1-(5-tert-Butyl-2-methoxy-phenyl)-3-{4-[2-(3-methoxy-phenyl)-pyrimidin-4-yloxy]-naphthalen-1-yl}-urea;

1-(5-tert-Butyl-2-methoxy-phenyl)-3-[4-(2-phenyl-pyrimidin-4-yloxy)-naphthalen-1-yl]-urea;

4-{4-[3-(5-tert-Butyl-2-methoxy-phenyl)-ureido]-naphthalen-1-yloxy}-pyrimidine-2-carboxylic acid methyl ester;

1-(5-tert-Butyl-2-methoxy-phenyl)-3-[4-(2-cyano-pyrimidin-4-yloxy)-naphthalen-1-yl]-urea; and 1-(5-tert-Butyl-2-methoxy-phenyl)-3-[4-(tetrahydro-pyran-4-yloxy)-naphthalen-1-yl]-urea or the pharmaceutically acceptable salts thereof.

2. A compound selected from the group consisting of:

1-[5tert-Butyl-3-(1,1-dioxo-1-lambda-6-isothiazolidin-2-yl)-2-methoxy-phenyl]-3-[4-(6-morpholin-4-ylmethyl-pyridin-3-yl)-naphthalen-1-yl]-urea;

N-(3-{3-[4-(2-Amino-6-methyl-pyrimidin-4-yloxy)-naphthalen-1-yl]-ureido}-5-tert-butyl-2-methoxy-phenyl)-methanesulfonamide;

N-(3-{3-[4-(2-Amino-pyrimidin-4-yloxy)-naphthalen-1-yl]-ureido}-5-tert-butyl-2-methoxy-phenyl)-methanesulfonamide;

N-(5-tert-Butyl-3-{3-[4-(2-cyano-pyrimidin-4-yloxy)-naphthalen-1-yl]-ureido}-2-methoxy-phenyl)-methanesulfonamide;

N-(5-tert-Butyl-2-methoxy-3-{3-[4-(tetrahydropyran-4-yloxy)-naphthalen-1-yl]-ureido}-phenyl)-methanesulfonamide N-(5-tert-Butyl-2-methoxy-3-{3-[4-(pyrimidin-4-yloxy)-naphthalen-1-yl]-ureido}-phenyl)-methanesulfonamide;

N-(5-tert-Butyl-2-methoxy-3-{3-[4-(2-methylamino-pyrimidin-4-yloxy)-naphthalen-1-yl]-ureido}-phenyl)-methanesulfonamide;

N-(5-tert-Butyl-2-methoxy-3-{3-[4-(6-methyl-2-methylamino-pyrimidin-4-yloxy)-naphthalen-1-yl]-ureido}-phenyl)-methanesulfonamide;

N-[5-tert-Butyl-3-(3-{4-[2-(cyclopropylmethyl-amino)-pyrimidin-4-yloxy]-naphthalen-1-yl}-ureido)-2-methoxy-phenyl]-methanesulfonamide;

N-[5-tert-Butyl-3-(3-{4-[2-(cyclopropylmethyl-amino)-6-methyl-pyrimidin-4-yloxy]-naphthalen-1-yl}-ureido)-2-methoxy-phenyl]-methanesulfonamide;

N-{5-tert-Butyl-2-methoxy-3-[3-(4-{2-[(tetrahydro-furan-2-ylmethyl)-amino]-pyrimidin-4-yloxy}-naphthalen-1-yl)-ureido]-phenyl}-methanesulfonamide; and N-(5-tert-Butyl-2-methoxy-3-{3-[4-(2-pyrrolidin-1-yl-pyrimidin-4-yloxy)-naphthalen-1-yl]-ureido}-phenyl)-methanesulfonamide or the pharmaceutically acceptable salts thereof.

3. A compound selected from the group consisting of:

1-[5-tert-butyl-2-(2-hydroxy-4-methyl-phenyl)-2H-pyrazol-3-yl]-3-[4-(2-morpholin-4-yl-ethoxy)-naphthalen-1-yl]-urea;

1-[5-tert-butyl-2-p-tolyl-2H-pyrazol-3-yl]-3-{4-[2-(hydroxy)ethoxy]-naphthalen-1-yl}-urea;

1-[5-tert-butyl-2-p-tolyl-2H-pyrazol-3-yl]-3-{4-[2-oxo-2-(morpholin-4-yl)-ethoxy]-naphthalen-1-yl}-urea; and 1-[5-tert-butyl-2-p-tolyl-2H-pyrazol-3-yl]-3-{4-[hydroxy]-naphthalen-1-yl}-urea or the pharmaceutically acceptable salts thereof.

4. A compound selected from the group consisting of:

1-(5-tert-Butyl-2-methoxy-phenyl)-3-[4-(2-isopropylamino-pyrimidin-4-yloxy)-naphthalen-1-yl]-urea;

1-(5-tert-Butyl-2-methoxy-phenyl)-3-[4-(2-cyclopropylamino-pyrimidin-4-yloxy)-naphthalen-1-yl]-urea;

1-(5-tert-Butyl-2-methoxy-phenyl)-3-{4-[2-(1-phenyl-ethylamino)-pyrimidin-4-yloxy]-naphthalen-1-yl}-urea;

1-(5-tert-Butyl-2-methoxy-phenyl)-3-(4-{2-[pyridin-3-ylmethyl)-amino]-pyrimidin-4-yloxy}-naphthalen-1-yl)-urea;

1-(5-tert-Butyl-2-methoxy-phenyl)-3-(4-{2-[pyridin-4-ylmethyl)-amino]-pyrimidin-4-yloxy}-naphthalen-1-yl)-urea;

1-(5-tert-Butyl-2-methoxy-phenyl)-3-(4-{2-[2-(4-methyl-piperazin-1-yl)-ethylamino]-pyrimidin-4-yloxy}-naphthalen-1-yl)-urea;

1-(5-tert-Butyl-2-methoxy-phenyl)-3-{4-[2-(2-pyrrolidin-1-yl-ethylamino)-pyrimidin-4-yloxy]-naphthalen-1-yl}-urea;

1-(5-tert-Butyl-2-methoxy-phenyl)-3-{4-[2-(2-oxo-tetrahydro-furan-3-ylamino)-pyrimidine-4-yloxy]-naphthalen-1-yl}-urea;

1-(5-tert-Butyl-2-methoxy-phenyl)-3-{4-[2-(tetrahydro-furan-3-ylamino)-pyrimidin-4-yloxy]-naphthalen-1-yl}-urea;

1-(5-tert-Butyl-2-methoxy-phenyl)-3-(4-{6-methyl-2-[(tetrahydro-furan-2-ylmethyl)-amino]-pyrimidin-4-yloxy}-naphthalen-1-yl)-urea;

1-(5-tert-Butyl-2-methoxy-phenyl)-3-{4-[2-(2-methoxy-1-methyl-ethylamino)-pyrimidin-4-yloxy]-naphthalen-1-yl}-urea;

2-(4-{4-[3-(5-tert-Butyl-2-methoxy-phenyl)-ureido]-naphthalen-1-yloxy}-pyrimidin-2-ylamino)-propionamide;

2-(4-{4-[3-(5-tert-Butyl-2-methoxy-phenyl)-ureido]-naphthalen-1-yloxy}-pyrimidin-2-ylamino)-N-methyl-propionamide;

2-(4-{4-[3-(5-tert-Butyl-2-methoxy-phenyl)-ureido]-naphthalen-1-yloxy}-pyrimidin-2-ylamino)-N,N-dimethyl-propionamide;

2-(4-{4-[3-(5-tert-Butyl-2-methoxy-phenyl)-ureido]-naphthalen-1-yloxy}-pyrimidin-2-ylamino)-N,N-dimethyl-acetamide 1-(5-tert-Butyl-2-methoxy-phenyl)-3-(4-{2-[1-(3-methoxy-phenyl)-ethylamino]-pyrimidin-4-yloxy}-naphthalen-1-yl)-urea;

1-(4-{2-[1-(2-Bromo-phenyl)-ethylamino]-pyrimidin-4-yloxy}-naphthalen-1-yl)-3-(5-tert-butyl-2-methoxy-phenyl)-urea;

1-(5-tert-Butyl-2-methoxy-phenyl)-3-{4-[2-(4-diethylamino-1-methyl-butylamino)-pyrimidine-4-yloxy]-naphthalen-1-yl}-urea;

1-(5-tert-Butyl-2-methoxy-phenyl)-3-{4-[2-(4-methoxy-benzylamino)-pyrimidin-4-yloxy]-naphthalen-1-yl}-urea;

1-(5-tert-Butyl-2-methoxy-phenyl)-3-{4-[2-(3-chloro-benzylamino)-pyrimidin-4-yloxy]-naphthalen-1-yl}-urea;

1-{4-[2-(Benzyl-methyl-amino)-pyrimidin-4-yloxy]-naphthalen-1-yl}-3-(5-tert-butyl-2-methoxy-phenyl)-urea;

1-(5-tert-Butyl-2-methoxy-phenyl)-3-(4-{2-[(2-dimethylamino-ethyl)-methyl-amino]-pyrimidin-4-yloxy}-naphthalen-1-yl)-urea;

1-[4-(2-Benzylamino-6-methyl-pyrimidin-4-yloxy)-naphthalen-1-yl]-3-(5-tert-butyl-2-methoxy-phenyl)-urea;

1-(5-tert-Butyl-2-methoxy-phenyl)-3-{4-[6-methyl-2-(1-phenyl-ethylamino)-pyrimidin-4-yloxy]-naphthalen-1-yl}-urea;

1-(5-tert-Butyl-2-methoxy-phenyl)-3-(4-{6-methyl-2-[(pyridin-2-ylmethyl)-amino]-pyrimidin-4-yloxy}-naphthalen-1-yl)-urea;

1-(5-tert-Butyl-2-methoxy-phenyl)-3-{4-[2-(2-dimethylamino-ethylamino)-6-methyl-pyrimidin-4-yloxy]-naphthalen-1-yl}-urea;

1-(5-tert-Butyl-2-methoxy-phenyl)-3-{4-[6-methyl-2-(2-morpholin-4-yl-ethylamino)-pyrimidin-4-yloxy]-naphthalen-1-yl}-urea;

1-(5-tert-Butyl-2-methoxy-phenyl)-3-[4-(2-dimethylamino-6-methyl-pyrimidin-4-yloxy)-naphthalen-1-yl]-urea;

N-(5-tert-Butyl-2-methoxy-3-{3-[4-(2-morpholin-4-yl-pyrimidin-4-yloxy)-naphthalen-1-yl]-ureido}-phenyl)-methanesulfonamide;

N-[5-tert-Butyl-2-methoxy-3-(3-{4-[2-(1-phenyl-ethylamino)-pyrimidin-4-yloxy]-naphthalen-1-yl}-ureido)-phenyl]-methanesulfonamide;

N-[5-tert-Butyl-2-methoxy-3-(3-{4-[6-methyl-2-(1-phenyl-ethylamino)-pyrimidin-4-yloxy]-naphthalen-1-yl}-ureido)-phenyl]-methanesulfonamide;

N-{5-tert-Butyl-2-methoxy-3-[3-(4-{2-[(pyridin-3-ylmethyl)-amino]-pyrimidin-4-yloxy}-naphthalen-1-yl)-ureido]-phenyl}-methanesulfonamide;

N-[5-tert-Butyl-3-(3-{4-[2-(2-dimethylamino-ethylamino)-pyrimidin-4-yloxy]-naphthalen-1-yl}-ureido)-2-methoxy-phenyl]-methanesulfonamide;

N-[5-tert-Butyl-3-(3-{4-[2-(2-dimethylamino-ethylamino)-6-methyl-pyrimidin-4-yloxy]-naphthalen-1-yl}-ureido)-2-methoxy-phenyl]-methanesulfonamide;

N-[5-tert-Butyl-2-methoxy-3-(3-{4-[2-(2-morpholin-4-yl-ethylamino)-pyrimidin-4-yloxy]-naphthalen-1-yl}-ureido)-phenyl]-methanesulfonamide;

N-[5-tert-Butyl-2-methoxy-3-(3-{4-[6-methyl-2-(2-morpholin-4-yl-ethylamino)-pyrimidine-4-yloxy]-naphthalen-1-yl}-ureido)-phenyl]-methanesulfonamide;

N-(5-tert-Butyl-3-{3-[4-(2-dimethylamino-pyrimidin-4-yloxy)-naphthalen-1-yl]-ureido}-2-methoxy-phenyl)-methanesulfonamide;

N-[5-tert-Butyl-2-methoxy-3-(3-{4-[2-(4-methyl-piperazin-1-yl)-pyrimidin-4-yloxy]-naphthalen-1-yl}-ureido)-phenyl]-methanesulfonamide;

N-(5-tert-Butyl-2-methoxy-3-{3-[4-(2-piperidin-1-yl-pyrimidin-4-yloxy)-naphthalen-1-yl]-ureido}-phenyl)-methanesulfonamide;

N-{5-tert-Butyl-3-[3-(4-{2-[(2-dimethylamino-ethyl)-methyl-amino]-pyrimidin-4-yloxy}-naphthalen-1-yl)-ureido]-2-methoxy-phenyl}-methanesulfonamide;

N-[5-tert-Butyl-2-methoxy-3-(3-{4-[2-(tetrahydrofuran-3-ylamino)-pyrimidin-4-yloxy]-naphthalen-1-yl}-ureido)-phenyl]-methanesulfonamide;

N-[5-tert-Butyl-2-methoxy-3-(3-{4-[2-(2-methoxy-1-methyl-ethylamino)-pyrimidin-4-yloxy]-naphthalen-1-yl}-ureido)-phenyl]-methanesulfonamide;

2-(4-{4-[3-(5-tert-Butyl-3-methanesulfonylamino-2-methoxy-phenyl)-ureido]-naphthalen-1-yloxy}-pyrimidin-2-ylamino)-N-methyl-propionamide;

2-(4-{4-[3-(5-tert-Butyl-3-methanesulfonylamino-2-methoxy-phenyl)-ureido]-naphthalen-1-yloxy}-pyrimidin-2-ylamino)-N,N-dimethyl-propionamide;

N-{5-tert-Butyl-2-methoxy-3-[3-(4-{2-[(pyridin-2-ylmethyl)-amino]-pyrimidin-4-yloxy}-naphthalen-1-yl)-ureido]-phenyl}-methanesulfonamide;

N-{5-tert-Butyl-2-methoxy-3-[3-(4-{6-methyl-2-[(tetrahydro-furan-2-ylmethyl)-amino]-pyrimidin-4-yloxy}-naphthalen-1-yl)-ureido]-phenyl}-methanesulfonamide;

N-(5-tert-Butyl-2-methoxy-3-{3-[4-(6-methyl-2-pyrrolidin-1-yl-pyrimidin-4-yloxy)-naphthalen-1-yl]-ureido}-phenyl)-methanesulfonamide;

2-(5-tert-Butyl-2-methoxy-3-{3-[4-(pyridin-4-yloxy)-naphthalen-1-yl]-ureido}-phenylamino)-thiazole-4-carboxylic acid ethyl ester;

2-(5-tert-Butyl-2-methoxy-3-{3-[4-(2-pyrrolidin-1-ylmethyl-pyridin-4-yloxy)-naphthalen-1-yl]-ureido}-phenylamino)-thiazole-4-carboxylic acid ethyl ester;

2-[5-tert-Butyl-2-methoxy-3-(3-{4-[2-(pyrrolidine-1-carbonyl)-pyridin-4-yloxy]-naphthalen-1-yl}-ureido)-phenylamino]-thiazole-4-carboxylic acid ethyl ester;

2-(5-tert-Butyl-2-methoxy-3-{3-[4-(2-methylaminomethyl-pyridin-4-yloxy)-naphthalen-1-yl]-ureido }-phenylamino)-thiazole-4-carboxylic acid ethyl ester;

2-(5-tert-Butyl-2-methoxy-3-{3-[4-(2-methylcarbamoyl-pyridin-4-yloxy)-naphthalen-1-yl]-ureido}-phenylamino)-thiazole-4-carboxylic acid ethyl ester;

2-(5-tert-Butyl-2-methoxy-3-{3-[4-(2-methylamino-pyridin-4-yloxy)-naphthalen-1-yl]-ureido}-phenylamino)-thiazole-4-carboxylic acid ethyl ester;

1-{5-tert-Butyl-2-methoxy-3-[4-(pyrrolidine-1-carbonyl)-thiazol-2-ylamino]-phenyl}-3-[4-(pyridin-4-yloxy)-naphthalen-1-yl]-urea;

1-[5-tert-Butyl-2-methoxy-3-(4-pyrrolidin-1-ylmethyl-thiazol-2-ylamino)-phenyl]-3-[4-(pyridin-4-yloxy)-naphthalen-1-yl]-urea;

2-(5-tert-Butyl-2-methoxy-3-{3-[4-(pyrimidin-4-yloxy)-naphthalen-1-yl]-ureido}-phenylamino)-thiazole-4-carboxylic acid ethyl ester;

2-(3-{3-[4-(2-Amino-pyrimidin-4-yloxy)-naphthalen-1-yl]-ureido}-5-tert-butyl-2-methoxy-phenylamino)-thiazole-4-carboxylic acid ethyl ester;

2-(5-tert-Butyl-2-methoxy-3-{3-[4-(2-methylamino-pyrimidin-4-yloxy)-naphthalen-1-yl]-ureido}-phenylamino)-thiazole-4-carboxylic acid ethyl ester;

2-[5-tert-Butyl-3-(3-{4-[2-(cyclopropylmethyl-amino)-pyrimidin-4-yloxy]-naphthalen-1-yl}-ureido)-2-methoxy-phenylamino]-thiazole-4-carboxylic acid ethyl ester;

2-(5-tert-Butyl-2-methoxy-3-{3-[4-(pyrimidin-4-yloxy)-naphthalen-1-yl]-ureido}-phenylamino)-thiazole-4-carboxylic acid (2-dimethylamino-ethyl)-methyl-amide;

1-{5-tert-Butyl-2-methoxy-3-[4-(pyrrolidine-1-carbonyl)-thiazol-2-ylamino]-phenyl}-3-[4-(pyrimidin-4-yloxy)-naphthalen-1-yl]-urea;

1-[5-tert-Butyl-2-methoxy-3-(4-pyrrolidin-1-ylmethyl-thiazol-2-ylamino)-phenyl]-3-[4-(pyrimidin-4-yloxy)-naphthalen-1-yl]-urea;

1-[5-tert-Butyl-2-methoxy-3-(4-pyrrolidin-1-ylmethyl-thiazol-2-ylamino)-phenyl]-3-[4-(2-isopropylamino-pyrimidin-4-yloxy)-naphthalen-1-yl]-urea;

1-{5-tert-Butyl-2-methoxy-3-[4-(pyrrolidine-1-carbonyl)-thiazol-2-ylamino]-phenyl}-3-{4-[2-(cyclopropylmethyl-amino)-6-methyl-pyrimidin-4-yloxy]-naphthalen-1-yl}-urea;

1-[5-tert-Butyl-2-methoxy-3-(4-pyrrolidin-1-ylmethyl-thiazol-2-ylamino)-phenyl]-3-{4-[2-(cyclopropylmethyl-amino)-6-methyl-pyrimidin-4-yloxy]-naphthalen-1-yl}-urea;

1-[5-tert-Butyl-3-(3-dimethylamino-pyrrolidin-1-ylmethyl)-2-methoxy-phenyl]-3-[4-(pyridin-4-yloxy)-naphthalen-1-yl]-urea;

1-[5-tert-Butyl-3-(3-dimethylaminomethyl)-2-methoxy-phenyl]-3-[4-(pyridin-4-yloxy)-naphthalen-1-yl]-urea;

1-[5-tert-Butyl-3-(3-dimethylamino-pyrrolidin-1-ylmethyl)-2-methoxy-phenyl]-3-[4-(2-dimethylaminomethyl-pyridin-4-yloxy)-naphthalen-1-yl]-urea;

1-[5-tert-Butyl-3-(3-dimethylamino-pyrrolidin-1-ylmethyl)-2-methoxy-phenyl]-3-[4-(pyrimidin-4-yloxy)-naphthalen-1-yl]-urea;

1-[4-(2-Amino-pyrimidin-4-yloxy)-naphthalen-1-yl]-3-[5-tert-butyl-3-(3-dimethylamino-pyrrolidin-1-ylmethyl)-2-methoxy-phenyl]-urea;

1-[4-(2-Amino-6-methyl-pyrimidin-4-yloxy)-naphthalen-1-yl]-3-[5-tert-butyl-3-(3-dimethylamino-pyrrolidin-1-ylmethyl)-2-methoxy-phenyl]-urea;

1-(5-tert-Butyl-3-dimethylaminomethyl-2-methoxy-phenyl)-3-{4-[2-(cyclopropylmethyl-amino)-pyrimidin-4-yloxy]-naphthalen-1-yl}-urea;

1-(5-tert-Butyl-3-dimethylaminomethyl-2-methoxy-phenyl)-3-{4-[2-(cyclopropylmethyl-amino)-6-methyl-pyrimidin-4-yloxy]-naphthalen-1-yl}-urea;

N-[5-tert-Butyl-2-methoxy-3-(3-{4-[2-(2-methoxy-phenyl)-pyrimidin-4-yloxy]-naphthalen-1-yl}-ureido)-phenyl]-methanesulfonamide;

4-{4-[3-(5-tert-Butyl-3-methanesulfonylamino-2-methoxy-phenyl)-ureido]-naphthalen-1-yloxy}-pyrimidine-2-carboxylic acid methyl ester;

1-[4-(2-Acetyl-pyrimidin-4-yloxy)-naphthalen-1-yl]-3-(5-tert-butyl-2-methoxy-phenyl)-urea;

N-(3-{3-[4-(2-Acetyl-pyrimidin-4-yloxy)-naphthalen-1-yl]-ureido}-5-tert-butyl-2-methoxy-phenyl)-methanesulfonamide;

1-(5-tert-Butyl-2-methoxy-phenyl)-3-{4-[2-(1-pyrrolidin-1-yl-ethyl)-pyrimidin-4-yloxy]-naphthalen-1-yl}-urea;

N-[5-tert-Butyl-2-methoxy-3-(3-{4-[2-(1-pyrrolidin-1-yl-ethyl)-pyrimidin-4-yloxy]-naphthalen-1-yl}-ureido)-phenyl]-methanesulfonamide; and 1-(2-methoxy-5-trimethylsilanyl-phenyl)-3-{4-[2-(cyclopropylmethyl-amino)-pyrimidin-4-yloxy]-naphthalen-1-yl}-urea or the pharmaceutically acceptable salts thereof.

5. A pharmaceutical composition comprising a pharmaceutically effective amount of a compound according to claim 1, 2, 3 or 4.

6. A method of treating a disease or condition selected from rheumatoid arthritis, Crohn's disease and ulcerative colitis comprising administering to a patient a therapeutically effective amount of a compound according to claim 1, 2, 3 or 4.

* * * * *